(12) United States Patent
Gale et al.

(10) Patent No.: US 7,089,938 B2
(45) Date of Patent: *Aug. 15, 2006

(54) PNEUMATIC OXYGEN CONSERVING DEVICE

(75) Inventors: Peter P. Gale, Bethlehem, PA (US); Stephen B. Krentler, Bethlehem, PA (US); Clyde W. Shuman, Allentown, PA (US)

(73) Assignee: Precision Medical, Inc., Northampton, PA (US)

( * ) Notice: Subject to any disclaimer, the term of this patent is extended or adjusted under 35 U.S.C. 154(b) by 58 days.

This patent is subject to a terminal disclaimer.

(21) Appl. No.: 10/770,049

(22) Filed: Feb. 2, 2004

(65) Prior Publication Data

US 2004/0154620 A1   Aug. 12, 2004

Related U.S. Application Data

(63) Continuation-in-part of application No. 10/040,190, filed on Oct. 19, 2001, now Pat. No. 6,752,152.

(51) Int. Cl.
*A61M 16/00* (2006.01)

(52) U.S. Cl. ............... 128/204.26; 128/205.24; 128/204.24; 128/204.25

(58) Field of Classification Search ........... 128/204.23, 128/204.26, 204.24, 204.25, 205.11, 205.22, 128/205.24; 251/28, 29
See application file for complete search history.

(56) References Cited

U.S. PATENT DOCUMENTS

| 435,367 | A | * | 8/1890 | Pratt | 251/29 |
|---|---|---|---|---|---|
| 687,273 | A | * | 11/1901 | Schoeffel | 251/29 |
| 917,740 | A | * | 4/1909 | Anderson | 134/492 |
| 2,378,047 | A | * | 6/1945 | Strange | 137/505.46 |
| 3,385,295 | A | * | 5/1968 | Beasley | 128/204.25 |
| 3,468,307 | A | * | 9/1969 | Cummins | 128/204.26 |
| 3,537,448 | A | * | 11/1970 | Liston | 128/200.21 |
| 3,580,137 | A | * | 5/1971 | Brandenberg | 91/50 |
| 4,054,133 | A | * | 10/1977 | Myers | 128/204.26 |
| 4,278,110 | A | * | 7/1981 | Price et al. | 137/805 |
| 4,575,042 | A | * | 3/1986 | Grimland et al. | 251/46 |
| 4,630,605 | A | * | 12/1986 | Pasternack | 128/205.24 |
| 5,000,174 | A | * | 3/1991 | Gray et al. | 128/205.24 |
| 5,050,593 | A | * | 9/1991 | Poon | 128/204.23 |
| 5,074,298 | A | * | 12/1991 | Arnoth | 128/204.18 |
| 5,259,375 | A | * | 11/1993 | Schuler | 128/205.24 |
| 5,360,000 | A | * | 11/1994 | Carter | 128/204.26 |
| 5,666,945 | A | * | 9/1997 | Davenport | 128/200.14 |
| 5,881,725 | A | * | 3/1999 | Hoffman et al. | 128/204.26 |
| 5,899,223 | A | * | 5/1999 | Shuman, Jr. | 137/505.25 |
| 6,116,242 | A |   | 9/2000 | Frye et al. | |
| 6,354,319 | B1 | * | 3/2002 | Mooney | 137/14 |
| 6,364,161 | B1 | * | 4/2002 | Pryor | 222/3 |
| 6,394,088 | B1 | * | 5/2002 | Frye et al. | 128/204.26 |
| 6,425,396 | B1 |   | 7/2002 | Adriance et al. | |
| 6,484,721 | B1 |   | 11/2002 | Bliss | |
| 6,568,391 | B1 | * | 5/2003 | Tatarek et al. | 128/204.26 |
| 6,612,307 | B1 | * | 9/2003 | Byrd | 128/204.26 |
| 6,752,152 | B1 | * | 6/2004 | Gale et al. | 128/204.26 |

* cited by examiner

*Primary Examiner*—Aaron J. Lewis
(74) *Attorney, Agent, or Firm*—Fish & Richardson P.C.; Richard P. Gilly

(57) ABSTRACT

A pneumatic oxygen conserving device uses a portion of gas exiting its main valve to interrupt delivery of the gas. Gas is dispensed upon inhalation and is interrupted by means of suitable pneumatic connections between the device's delivery system and its sensing system.

43 Claims, 15 Drawing Sheets

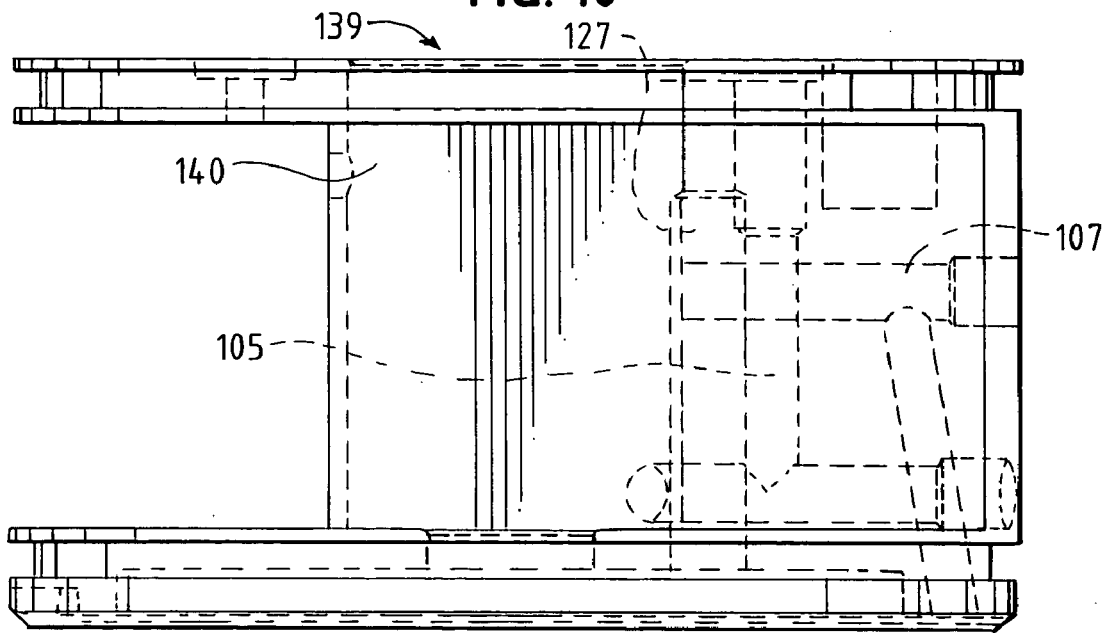
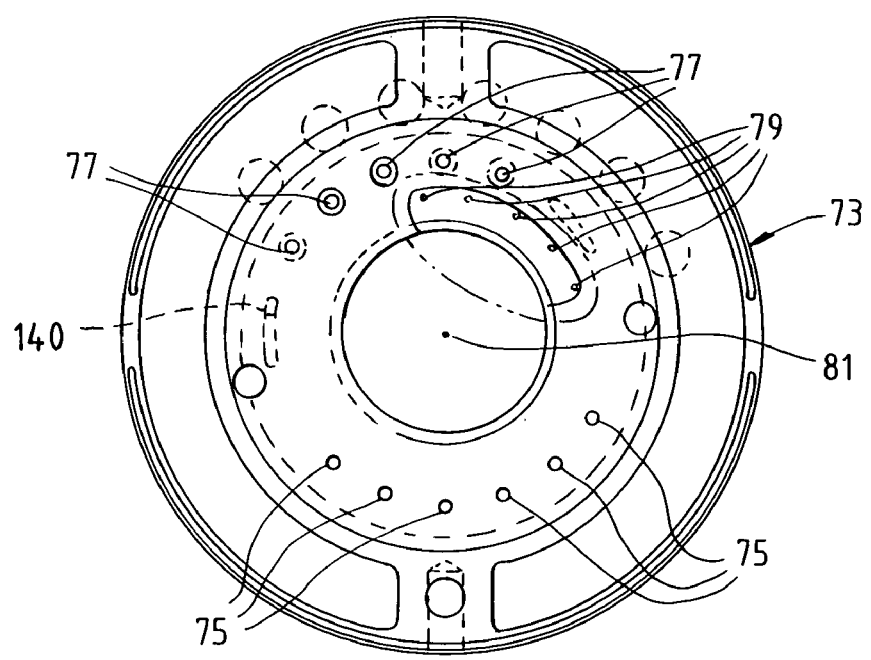

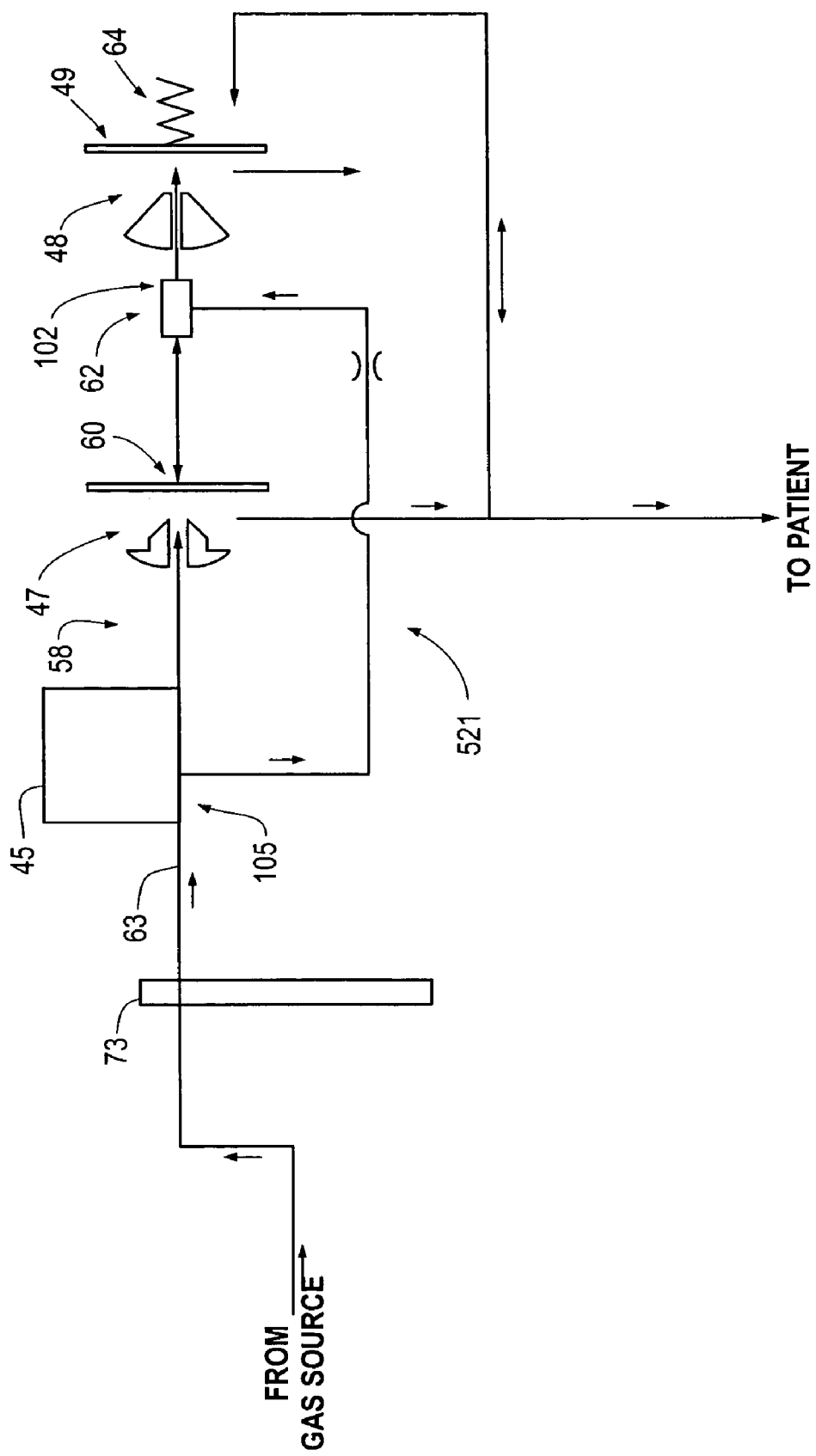

PNEUMATIC OXYGEN CONSERVING DEVICE

RELATED APPLICATION

This application is a continuation-in-part of application Ser. No. 10/040,190, filed Oct. 19, 2001 now U.S. Pat. No. 6,752,152.

FIELD OF THE INVENTION

This invention relates generally to gas delivery systems and, more particularly, to a system for delivering oxygen which includes an oxygen conserving device or oxygen conserver.

BACKGROUND OF THE INVENTION

Gas delivery systems typically include a source of gas, such as oxygen, a regulator for reducing the source pressure of the oxygen to a pressure more suitable for use within the delivery system, and a gas line, typically a cannula, for delivering oxygen from the delivery system to the person. Oxygen delivery systems are used not only in hospitals and health care institutions, but also in home-health care and by ambulatory persons requiring oxygen for any number of reasons. Wherever such oxygen delivery systems are used, it is frequently desirable to increase the life of the oxygen supply. This is especially the case in home-based or ambulatory settings where the supply of oxygen is often an oxygen bottle or other relatively finite oxygen source.

To increase the life of the oxygen supply, oxygen conserving devices, also known as oxygen conservers, are frequently used. These conserving devices generally interrupt the flow of oxygen delivered to the person at regular intervals, thereby reducing the rate of oxygen consumption.

Conservers are generally of two types, those which operate electronically, and those which operate pneumatically. Each of these types suffers from various drawbacks and disadvantages. For example, electronic conservers require a power source, generally a battery, in order to operate, thus necessitating periodic replacement or recharging of the power source.

Electronic oxygen conservers sometimes have further disadvantages related to durability and cost.

Pneumatic oxygen conservers are those which make use of the pressurized gas and its flow within the conserver to intermittently block the delivery of gas to the person. Although such pneumatic conservers generally dispense with the need for power sources and complex electronics, they are oftentimes bulkier.

A further disadvantage of pneumatic systems is that they generally require more complex gas lines or cannulas in order to operate. Examples of such pneumatic conservers and their associated dual-lumen cannulas are disclosed in Myers U.S. Pat. No. 4,044,133 and Carter U.S. Pat. No. 5,360,000. One lumen of the cannula is for supplying oxygen to the person wearing the cannula, whereas the other lumen generally connects to a sensing port on the conserver. The pneumatic conserver generally responds to changes in the pressure in the sensing lumen to provide oxygen to the person during inhalation and to interrupt the flow of oxygen to the person in response to exhalation (when oxygen is typically not needed). Unfortunately, dual lumen cannulas are more difficult to obtain, more expensive, bulkier, and generally heavier than the standard, single lumen cannulas used in electronic conservers and many other medical devices.

As a result of these and other drawbacks, pneumatic oxygen conserving devices have not enjoyed widespread use despite certain advantages of such pneumatic conservers over electronic ones.

The various attempts to overcome the drawbacks of pneumatic conservers have had mixed results and have generated their own drawbacks and disadvantages. For example, although the pneumatic oxygen conserver disclosed in Hoffman U.S. Pat. No. 2,881,725, makes use of a single-lumen cannula, the device disclosed therein does not generally deliver oxygen in a manner consistent with the oxygen consumption profiles of a person breathing through a cannula. In other words, it is desirable for oxygen delivery from a conserving device to match a person's needs for oxygen as closely as possible.

There is a need, therefore, for a pneumatic oxygen conserving device which can be used as part of an oxygen delivery system, and which overcomes the disadvantages of current oxygen delivery systems.

SUMMARY OF THE INVENTION

According to one aspect of the invention, a conserving device includes a delivery system and a sensing system. The delivery system is adapted to be pneumatically connected to a source of gas for delivery to a person and has components which allow it to operate to dispense gas intermittently from the source of gas to such person. The sensing system is likewise adapted to be in pneumatic communication with the person so that when the person inhales, the sensing system can detect the corresponding pressure drop. The conserving device includes a suitable pneumatic communication between the sensing system and the delivery system so that the gas, when dispensed, causes the deliver system to interrupt the dispensing of the gas thereafter.

According to another aspect of the present invention, a delivery system includes a main valve and the sensing system includes a sensing valve. A first pneumatic connection extends between the source of gas and the main valve to bias the main valve toward its closed position. A second pneumatic connection extends between the main valve and the sensing valve to receive a portion of the gas exiting the main valve and transmit a sufficient pressure to the sensing valve to close the sensing valve. Upon closing of the sensing valve, the gas from the first pneumatic connection closes the main valve which, in turn, interrupts delivery of the gas to the patient.

The pneumatic connection between the delivery system and the sensing system of the device can assume any of a variety of sizes, dimensions, or configurations. In one particular version of the invention, a pneumatic connection between the source of gas and the main valve comprises a pressure line which biases the main valve toward the closed position. In another version, a pneumatic connection in the form of a sensing passage can be provided between the main valve and the sensing valve to receive a portion of the gas exiting the main valve, although, again, such pneumatic connections may take alternate forms.

BRIEF DESCRIPTION OF THE DRAWINGS

The invention will be better understood by reference to the attached drawing. It is understood that the drawing is for illustrative purposes only and is not necessarily drawn to scale. In fact, certain features of the drawing are shown in more detail for purposes of explanation and clarification. In the drawing:

FIGS. 9 and 10 are two side views of the component of FIGS. 7 and 8;

FIGS. 11, 12, and 13 are top, bottom, and side sectional views, respectively, of another component of the oxygen conserver of the present invention;

FIG. 19 is a schematic representation of a fourth alternative embodiment according to the present invention.

DETAILED DESCRIPTION OF THE PREFERRED EMBODIMENTS

Figure 1:
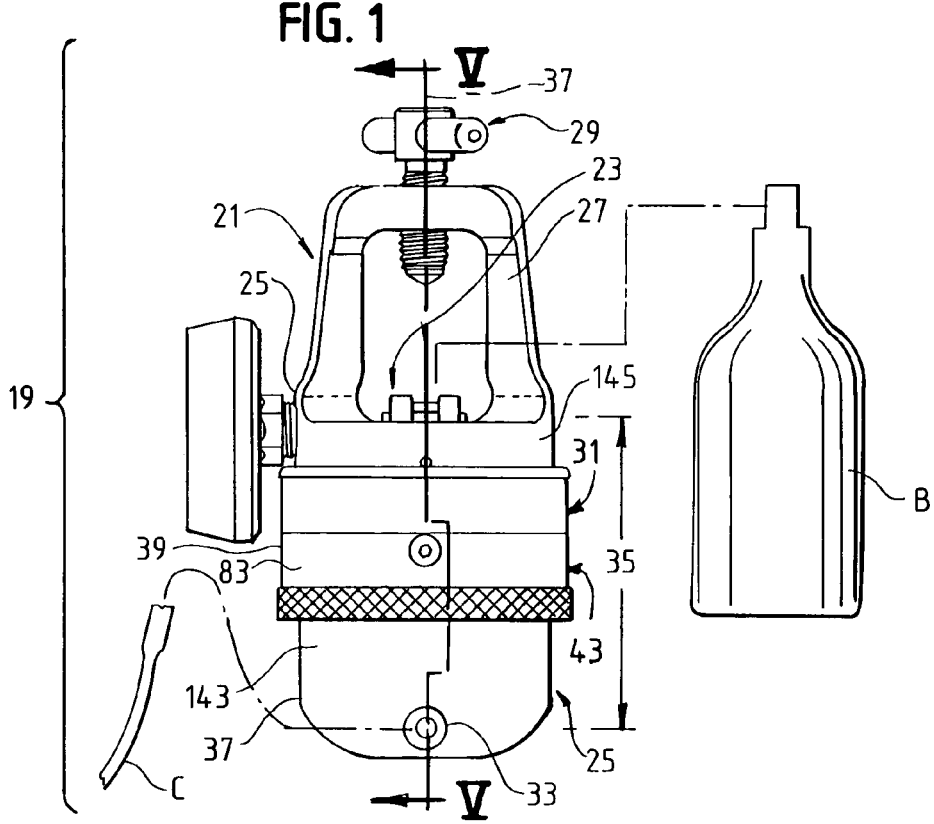
FIG. 1 a side elevational and partly schematic view of an apparatus for delivering oxygen according to the present invention.

Referring now generally to FIG. 1, an apparatus 19 for delivery of oxygen includes an oxygen conserving device or conserver 21 which is pneumatic in design, that is, it makes use of pressurized gas to operate. Conserving device or conserver 21 is connected to gas source B in order to deliver gas to the person intermittently. Oxygen conserving device 21 has the advantage of being usable with any of a variety of standard, single-lumen cannulas, such as that shown by reference numeral C.

Oxygen conserving device 21 has a regulator inlet 23 defined at a suitable location in housing 25 of conserving device 21, preferably toward one of the ends thereof. Inlet 23 is adapted to connect to any of a variety of gas sources, such as bottle of oxygen B under a predetermined pressure. Conserving device 21 includes suitable means for connecting or securing gas source B pneumatically to regulator inlet 23. In this case, such securing means comprises a yoke 27 with a manually adjustable locking handle 29.

Pressurized gas, preferably oxygen, flows from gas source B into regulator inlet 23 and through main body 31 of the conserving device 21. During such travel the gas is acted upon by various valves, passages and other components to be described subsequently. The gas ultimately exits delivery outlet 33 in pulses which are optimally sized and optimally timed, thereby conserving oxygen while supplying such oxygen in the amounts and intervals required by the person receiving oxygen.

Figure 2:
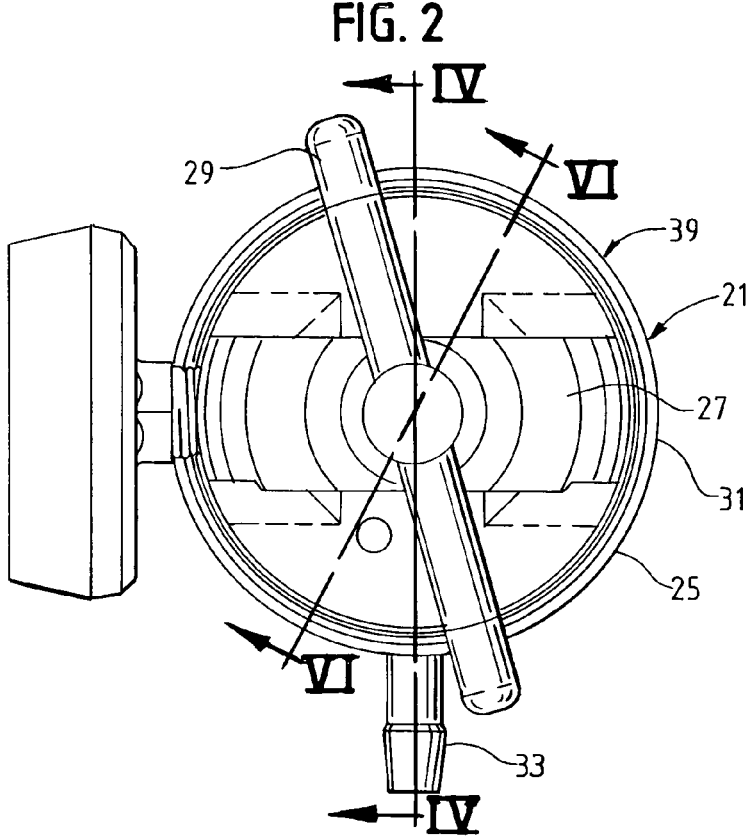
FIG. 2 is a top plan view of the oxygen conserving device of the apparatus shown in FIG. 1.

The passages, chambers, and other components within main body 31 are arranged so as to minimize distance 35 between regulator inlet 23 and delivery outlet 33, thereby rendering conserving device 21 relatively compact. As seen in FIGS. 1 and 2, main body 31 is substantially cylindrical and has a central longitudinal axis 37 about which exterior surface 39 of main body 31 is substantially symmetric.

Referring now more particularly to FIGS. 3–6, the major components or systems of conserving device 21 operate and are interconnected as follows. Regulator 41 reduces the pressure of the gas from gas source B to a delivery pressure. A flow-rate selector 43 (FIGS. 4–6) determines the rate at which the gas, at delivery pressure, flows into a rechargeable reservoir 45. Main valve 47 causes gas to be dispensed from reservoir 45 intermittently and in response to certain pressures exerted on main valve 47. Movements of a sensing valve 49 occur in part by inhalation of the person using the conserving device 21, as well as by flow of gas through a pressure line 105 in cooperation with backflow through a sensing passage 50 of device 21, as will be explained in more detail subsequently.

In general terms, then, conserving device 21 includes a delivery system 32 which has certain passages and valves in pneumatic communication with the reservoir 45 (including main valve 47, for example), with other systems, and with the person, so as to open and close reservoir outlet 87 and dispense gas intermittently from reservoir 45 to the person. Conserving device also includes certain passages and valves (including sensing valve 49, for example) which form sensing system 48, which is in pneumatic communication with the person to receive gas to detect a pressure drop upon inhalation by the person. Sensing system 48 is likewise in pneumatic communication with delivery system 32 to cause the delivery system 32 to open reservoir outlet 87 in response to detecting the pressure drop mentioned above. A gas control system 90 is pneumatically connected to the gas source, to delivery system 32, and to sensing system 48.

Certain passages of gas control system 90 (including pressure line 105 and sensing passage 50, for example) are sized and established so that gas control system 90 increases pressure in the sensing system 48 when gas control system 90 receives gas from delivery system 32 and causes reservoir outlet 87 to close and thereby interrupt the delivery of gas to the person, in response to the increased pressure in sensing system 48.

The systems 32, 48, and 90 are operatively interconnected so that an oxygen-rich pulse is delivered to the person during the first half of the person's inspitory cycle, that is, the person's inhalation, which time period has been identified as a useful and desirable moment for the person to receive oxygen. Furthermore, delivery of the oxygen pulse is preferably performed through any standard single-lumen cannula rather than the dual-lumen cannula typically found in pneumatic oxygen conserving devices.

Sensing passage 50 is pneumatically connected to main valve 47 and sensing valve 49 so as to better conserve oxygen, while at the same time maintaining a desirable oxygen delivery profile and thus not depriving the person of needed oxygen. In this embodiment, sensing passage 50 includes an optional check valve 51. Check valve 51, in combination with other components of conserving device 21, operates to interrupt the flow of oxygen independently of exhalation of their patient.

By filling reservoir 45 at a rate selected by flow-rate selector 43, a corresponding "flow minute volume", that is, a volume of oxygen per minute, is delivered to the patient generally without regard to the number of breaths taken by the patient per minute. In other words, the pneumatic connections of reservoir 45 allow the conserving device 21 to be self-regulating: more rapid breathing by the person will deliver smaller but more frequent pulses of oxygen, whereas less rapid breathing will deliver larger and correspondingly less frequent pulses of oxygen, in either event, resulting in the same volume of gas delivered per minute.

Regulator 41 delivers gas from gas source B at a predetermined delivery pressure by means of a disk 53 biased by suitable means, here shown as multiple springs 55. Gas enters regulator 41 through regulator orifice 57, travels through various passages to the back side 59 of disk 53 and thereby overcomes the biasing of springs 55 to a sufficient degree to create the desired delivery pressure at the back side 59.

Operation and construction of regulator 41 is generally well-known in the art, one suitable example being disclosed in U.S. Pat. No. 5,899,223, of common assignee, the teachings of which are incorporated herein by reference.

Figure 4:
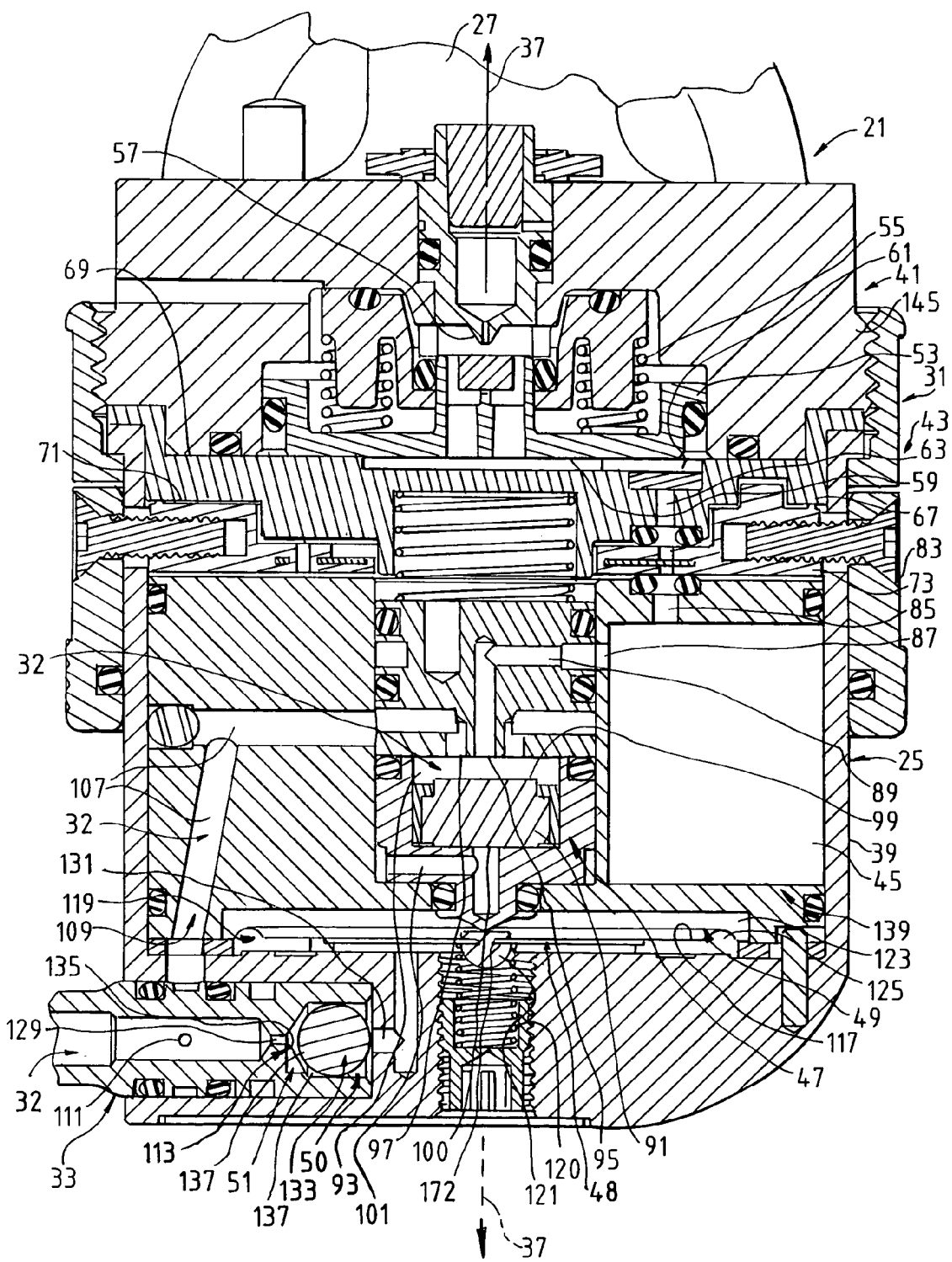
FIG. 4 is a cross-sectional view of the conserving device taken along line IV—IV of FIG. 2.
Figure 5:
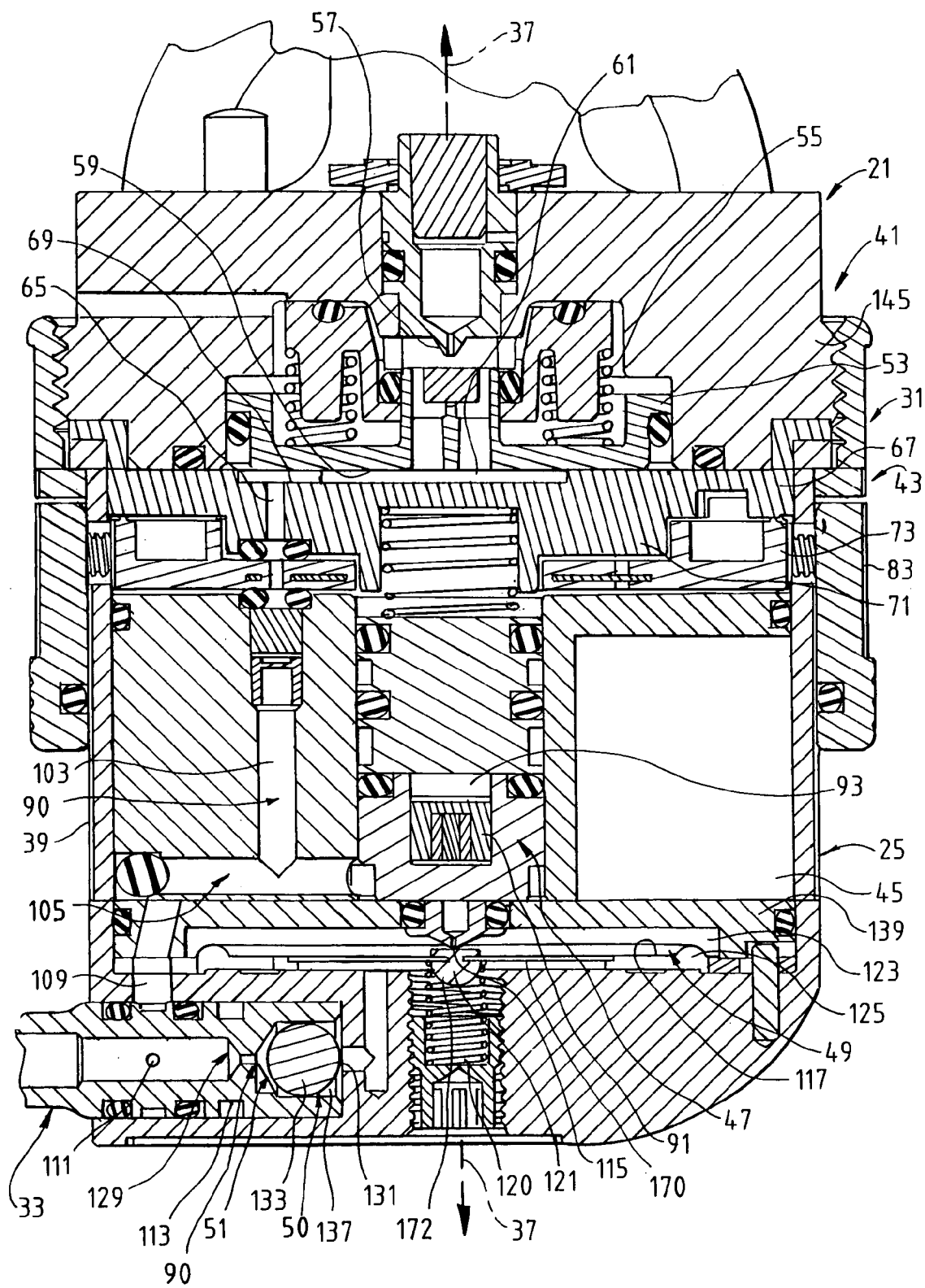
FIG. 5 is a cross sectional view taken along line V—V of FIG. 1.

Gas at a desired delivery pressure, 50 psi in this preferred embodiment, is present in region 61 adjacent to backside 59 of disk 53. From regions 61, gas flows through flow-rate selector 43 through two passages: a variable-rate passage 63 (FIG. 4) and a pressure passage 65 (FIG. 5). Passages 63, 65 extend, in part, through flow-rate selector cap 67. Cap 67 has a surface 69 which opposes regulator 41 and forms part of region 61 containing gas at the delivery pressure. Cap 67 includes a second surface 71 opposite surface 69. Surface 71 is shaped to receive orifice plate 73 in a substantially opposing relationship thereto. Orifice plate 73, shown in more detail in FIGS. 11–13, includes three sets of orifices 75, 77 and 79 extending between opposite planar surfaces of orifice plate 73. The orifices of each set 75, 77, and 79 are spaced at predetermined angles from each other. Each set of orifices is located at a corresponding radial distance from center 81 of orifice plate 73.

Orifice set 75 comprise the so-called variable rate orifices by including orifices of diameters varying between 0.010 to 0.004 inches. Orifice set 77 comprise the so-called constant rate orifices by including orifices having the same diameter, preferably about 0.036 inches. Orifice set 79 comprises vent orifices for allowing gas to escape main body 31 at predetermined rates to improve the delivery of oxygen to the person.

Orifice plate 73 is coaxially mounted to cap 67 and is rotatable relative thereto so that the user can position a selected one of the variable rate orifices 75 into variable rate passage 63 to deliver gas through such passage at the desired rate. Similarly, the set of constant rate orifices 77 is positioned so that a selected one of such orifices is interposed within pressure passage 65 whenever gas is flowing through the variable rate passage 63.

Flow-rate selector 43 is provided with a ring or knob 83 to enable the person to readily rotate orifice plate 73 to the desired flow-rate setting. Suitable indicia (not shown) can be provided to indicate the amount of gas flowing through the variable-rate passage. In this preferred embodiment, the volume passing through the variable rate passage 63 is indicated by reference numerals without units, rather than as liters per minute, that is, level 1, level 2, level 3 level 4, etc.

Variable-rate passage 63 is pneumatically connected to reservoir inlet 85 of reservoir 45. A reservoir outlet 87 is also defined in reservoir 45, which outlet 87, in turn, leads to passage 89. Passage 89, in turn, extends to and pneumatically communicates with main valve 47.

Main valve 47 is formed by having a movable element, preferably a piston 91, which reciprocates within a chamber 93. Chamber 93 has a chamber inlet 95 at the end of passage 89, thereby in pneumatic communication with reservoir outlet 87. Chamber 93 also has a chamber outlet 97 defined therein. Chamber inlet 95 and chamber outlet 97 are preferably located to one side 99 of piston 91. On the opposite side 100 of piston 91, a pressure inlet 101 (FIG. 4) is defined in chamber 93. Pressure inlet 101 is pneumatically connected to constant rate passage 65 in cap 67 by means of intermediate passage 103, as best seen in FIG. 5.

The pressure passage 65, intermediate passage 103, and pressure inlet 101 together comprise a pressure line 105 which exerts sufficient pressure on side 100 of piston 91 to urge piston 91 upward under certain pressure conditions. When piston 91 is urged upwardly to its limit position, main valve 47 is in the closed position, that is, reservoir outlet 87 is closed, thereby permitting reservoir 45 to become filled with gas flowing through reservoir inlet 85. The upper position of piston 91, during which it closes reservoir outlet 87, is shown in phantom lines in FIG. 4.

Conversely, when piston 91 reciprocates to its lower position shown in solid lines, reservoir outlet 87 is open, permitting gas to flow from reservoir 45 for delivery to the patient. More particularly, gas for delivery to the user flows from chamber outlet 97 through delivery passage 107 (FIG. 4) which terminates at a delivery end 109 adjacent to delivery outlet 33. Gas exits delivery end 109 and enters delivery outlet 33 through a plurality of side bores 111 defined in a fitting 113. Fitting 113 is, in turn, connected to single-lumen cannula C (FIG. 1) for delivery to the user.

The foregoing has described the main components of conserving device 21 and how they deliver gas to the user. It will now be explained how the conserving device 21 interrupts gas delivery, that is, conserves gas by delivering it when called for by the person. Pressure line 105 communicates not only with chamber 93 of main valve 47 but also with sensing valve 49 through port 115. Sensing valve 49 includes a sensing chamber 119 defined within main body 31 in communication with a port 115. A sensing element 117 is disposed within sensing chamber 119. Sensing element 117 preferably comprises a diaphragm with a suitable reinforced portion 121 which opposes port 115. Sensing element 117 is biased against port 115 by means of spring 120.

Figure 6:
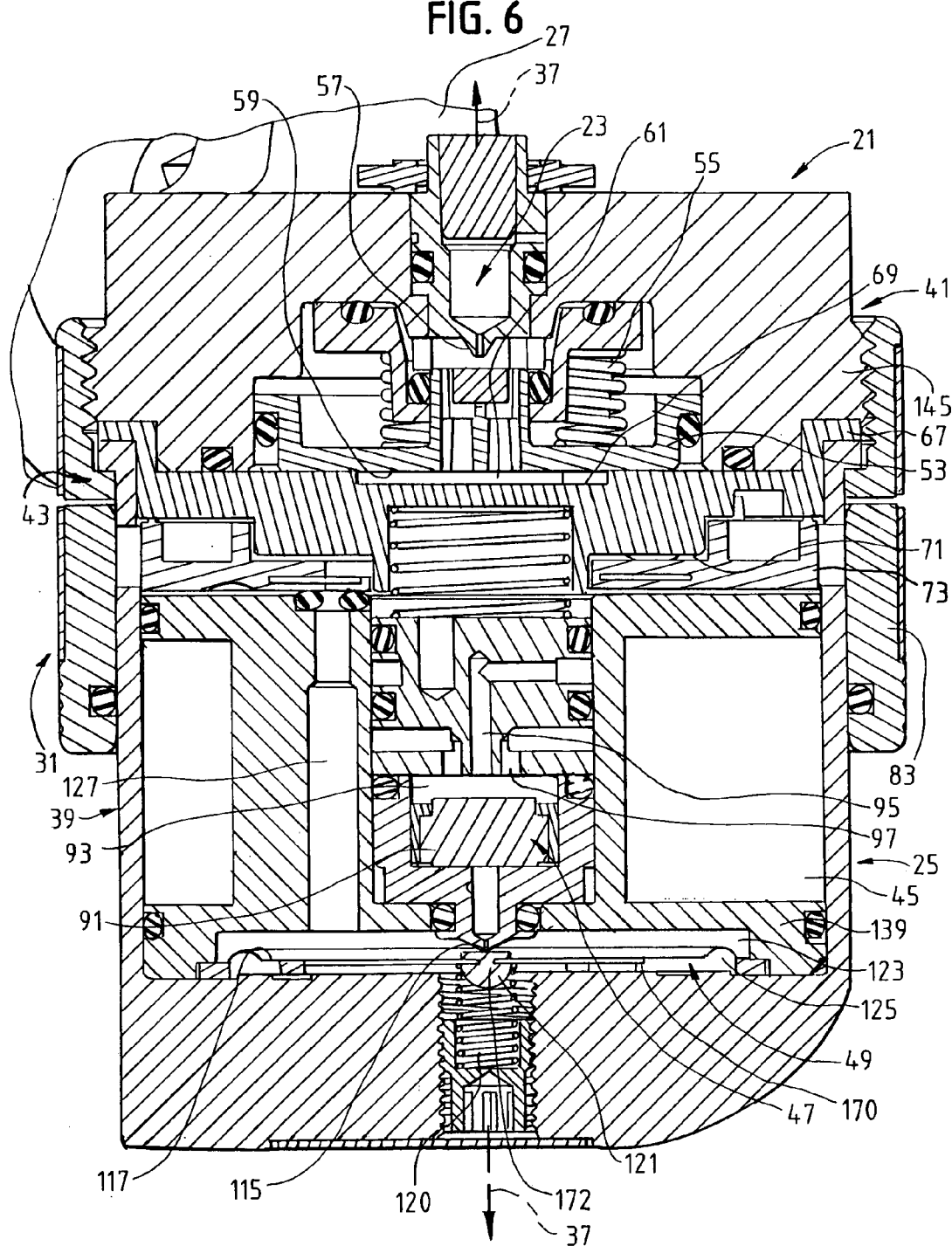
FIG. 6 is a cross sectional view taken along line VI—VI of FIG. 2.
Figure 7:
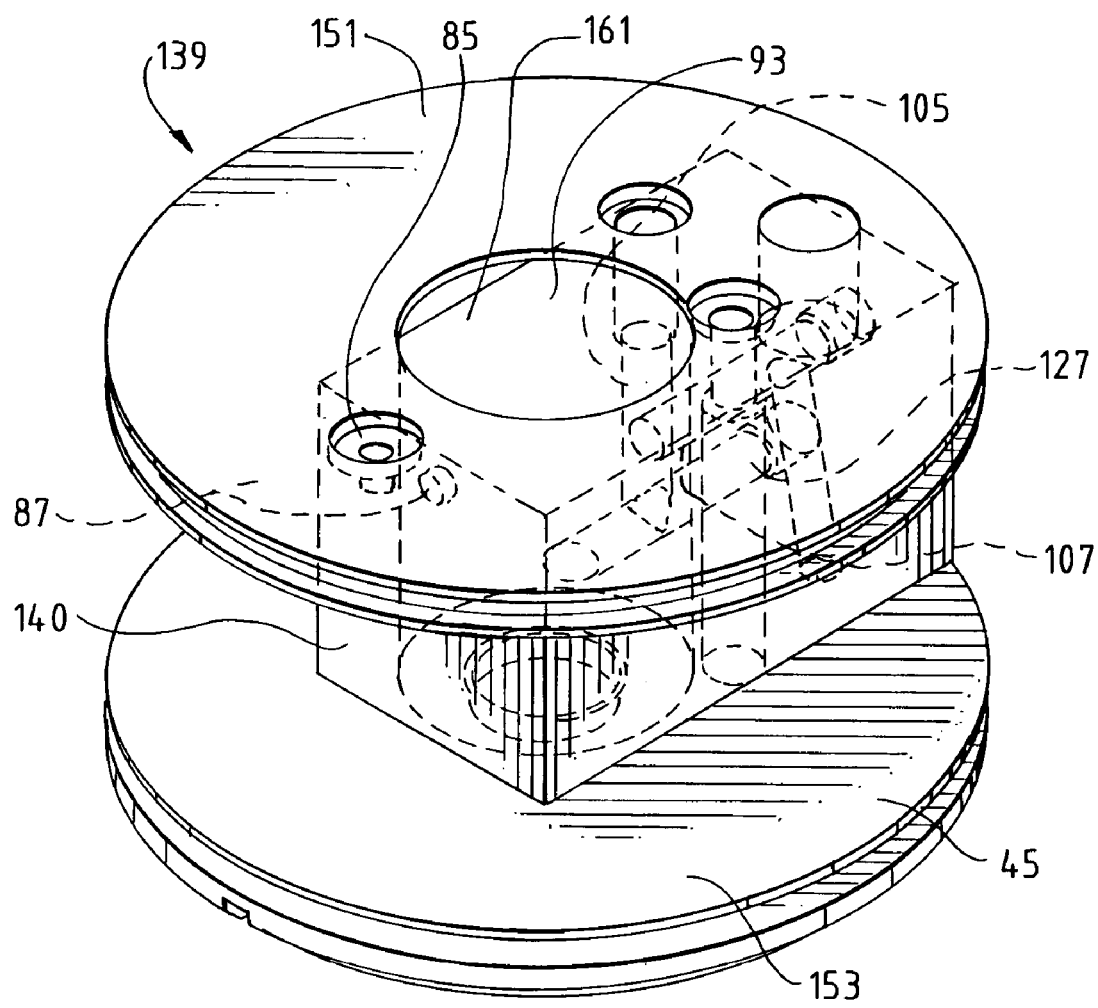
FIGS. 7 and 8 are perspective and top plan views, respectively, of one of the components of the conserving device of FIGS. 2 through 6.
Figure 8:
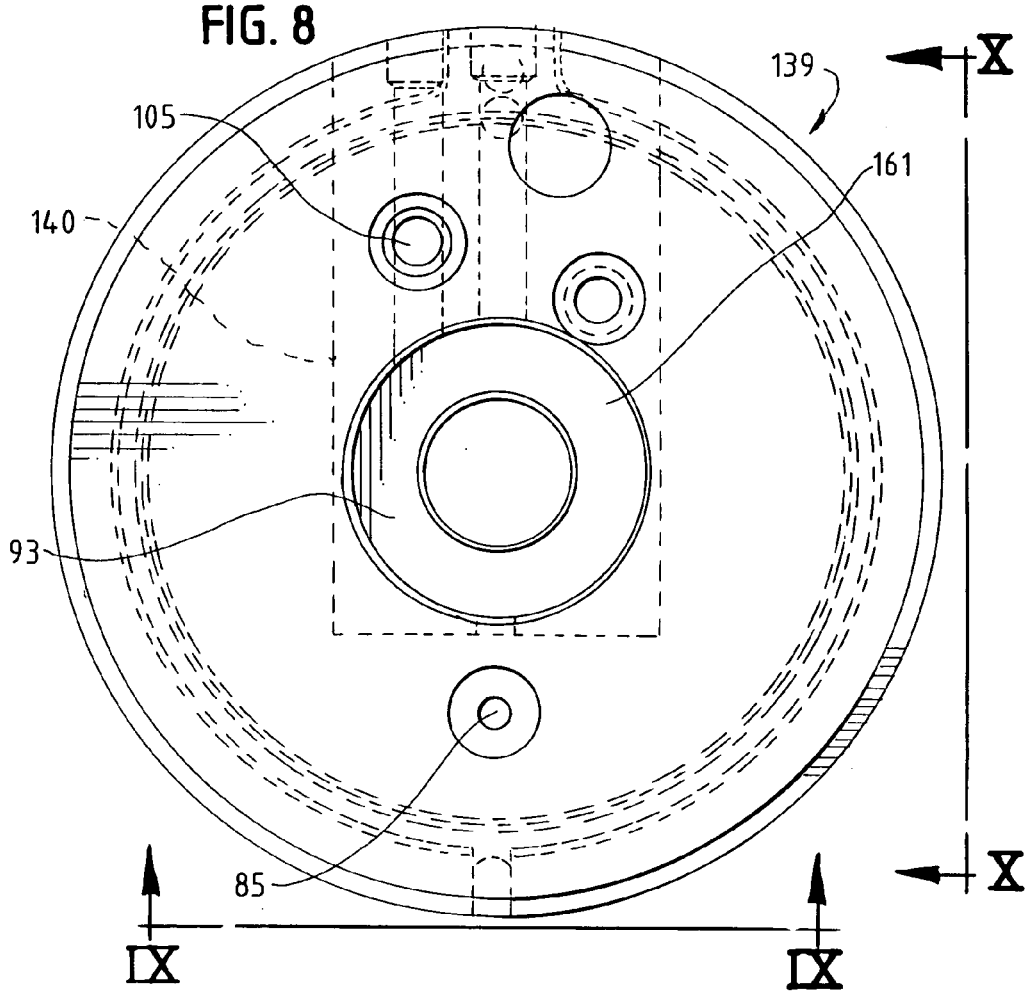
Figure 9:
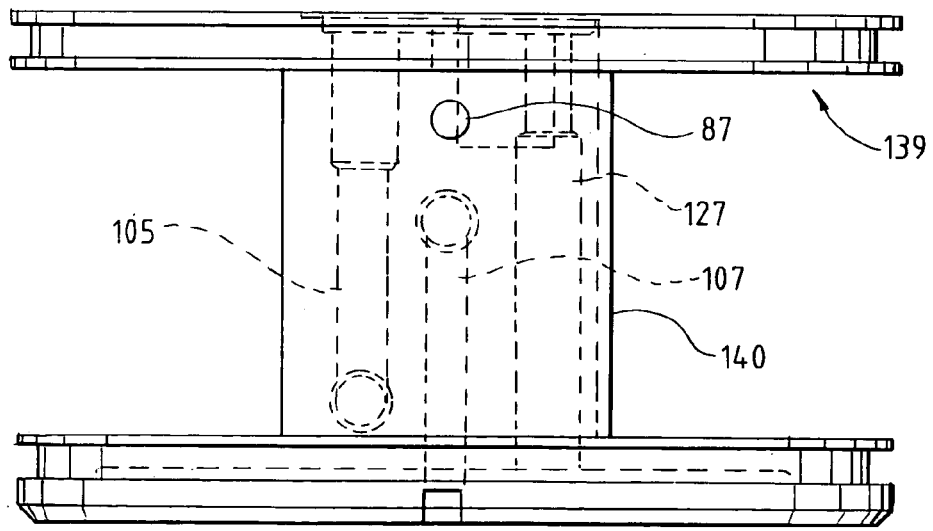

Sensing element 117 divides sensing chamber 119 into two regions: a first region 123 in pneumatic communication with port 115, and a second region 125 in pneumatic communication with delivery outlet 33. Region 123, as seen in FIG. 6, has a vent to atmosphere 127 extending from it.

When sensing valve 49 is in the closed position, sensing element 117 is positioned to seal port 115. Conversely, when sensing valve 49 is open, sensing element 117 is spaced from port 115, thereby allowing gas from pressure line 105 to flow therethrough. When gas flows from pressure line 105 through port 115, such gas is vented through the vent to atmosphere 127 at a predetermined rate.

In this embodiment, sensing passage 50 is disposed between and in pneumatic communication with delivery outlet 33 and sensing valve 49. Sensing passage 50 has a first opening or subpassage 129 communicating with delivery outlet 33 and a second opening or subpassage 131 communicating with region 125 of sensing valve 49. First opening 129 is sized so that the pressure of gas being dispensed through delivery outlet 33 is not immediately or fully transmitted to sensing valve 49. Otherwise stated, the cross-sectional area of opening 129 is relatively smaller than the cross-sectional areas adjacent such opening 129, creating a corresponding restriction at a medial location in sensing passage 50. Optional check valve 51 increases assurances that appropriate pressures are transmitted from gas under delivery to sensing valve 49. Check valve 51 includes a check element 133 received in a chamber 137 of check valve 51. Check element 133 is movable between the two openings 129, 131 in response to pressure differences between opposing sides of check element 133. When check element 133 abuts second opening 131, opening 131 is substantially sealed. However, when check element 133 abuts first opening 129, a complete seal is not formed because a counterbore 135 extends from opening 131 into chamber 137. Check element 133 and counterbore 135 are suitably formed so that counterbore 135 is not sealed by the outer surface of check element 133 even when check element 133 is brought against first opening 129.

Pressure line 105 terminates in delivery outlet 33 at a location so that line 105 communicates with first opening 129 of check valve 51. Otherwise stated, gas exits pressure line 105 on the "delivery side" of check valve 51.

In operation, when the user inhales through cannula C, a lower than ambient condition or vacuum is transmitted through cannula C to the delivery outlet 33. The resulting vacuum passes through sensing passage 50 and acts to open sensing valve 49. In this embodiment, check element 133 moves toward opening 129 a sufficient amount to unseat it from opening 131. By virtue of counterbore 135, sensing passage 50 comprises a continuous air passage between region 125 of sensing valve 49, that is, "on the delivery side" of sensing element 117, such air passage extending through check valve 51 and into cannula C. The vacuum created by inhalation thus draws air from region 125 of sensing valve 49. The flow of air in this manner is sufficient to overcome the bias of spring 120 and separate sensing element 117 from port 115.

Once port 115 is open, gas from the pressure line 105 flows out port 115 and escapes the main body 31 of the device 21 through vent to atmosphere 127. Although gas exiting port 115 is being vented to atmosphere, a certain amount of back pressure is maintained in region 123 of sensing chamber 119 by virtue of venting orifices 79 which slow the flow of gas out of the vent to atmosphere 127. Vent orifices 79 have sizes selected to maximize the oxygen delivery profile corresponding to respective volumes of the variable-rate orifice set 75. Otherwise stated, the back pressure created by the venting orifices 79 generally keeps port 115 open for a slightly longer period which, in turn, continues delivery of oxygen for a correspondingly longer period as well.

When a sufficient amount of gas from the pressure line 105 escapes through vent to atmosphere 127, the pressure which previously kept the piston 91 in sealing engagement with reservoir outlet 87 is sufficiently reduced so that piston 91 reciprocates away from reservoir outlet 87 to open outlet 87. Once reservoir outlet 87 is open, gas stored in reservoir 45 under a predetermined pressure escapes through outlet 87 into chamber 93 of main valve 47 and then exits chamber 93 through chamber outlet 97 to enter delivery passage 107. From delivery passage 107, gas exits delivery outlet 33 and flows to the person through cannula C.

Significantly, as gas exits delivery passage 107 through delivery end 109, the pressure of the gas during delivery is felt in sensing passage 50. As a result, check element 133 moves against and seals opening 131. The seating of check element 133 in this fashion returns region 125 of sensing valve 49 to a higher pressure, preferably approaching atmospheric, such pressure being sufficient to allow spring 120 to reseat sensing element 117 against port 115. Once port 115 has been resealed by sensing element 117, pressure line 105 repressurizes region 123 of sensing valve 149 and, importantly, the region adjacent to the lower side of piston 91. Bottom side 100 of piston 91 has a sufficiently large surface area so that once gas pressure reaches a certain level in the region adjacent to surface 100, piston 91 reseats in the upper, closed position to reseal reservoir outlet 87.

The sealing of reservoir outlet 87 interrupts the flow of oxygen being delivered to the patient. In this way, pulses of oxygen are delivered to the person, such pulses substantially corresponding to the release of gas stored in reservoir 45. In addition, the size and length of the oxygen pulse is regulated in substantial part by the outflow of the pulse from the device, rather than by exhalation of the person, with the result that the oxygen pulse better matches the demand for oxygen under most circumstances. As such, conservation of oxygen is accomplished while also fulfilling the recommended oxygen delivery profiles of persons using the device.

Figure 14:
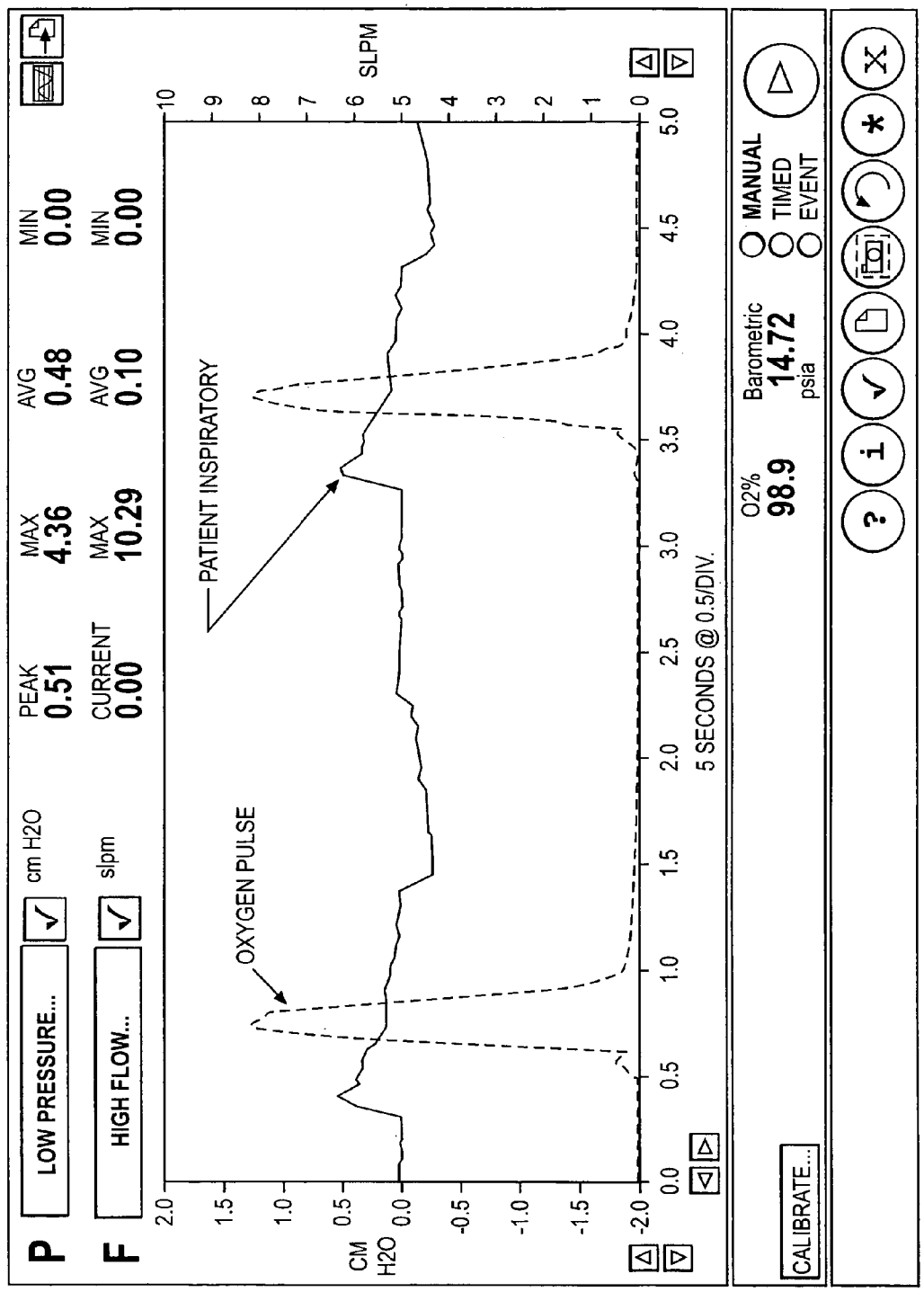
FIG. 14 is a graph of the operation of the device according to the present invention.

One such oxygen delivery profile has been graphed in FIG. 14. In general terms, the solid line charts the person's or the patient's inspiratory cycle, that is, the inhalation and exhalation of the patient. The onset of inhalation or inspiration is shown as a slight spike occurring approximately at 0.4 seconds and again at 3.4 seconds, and measured as an increase in pressure in cannula C. It has been found desirable to deliver as much oxygen, that is, as much of the pulse as possible, within the first half second of inspiration. The device 21, according to the present invention, generally accomplishes such goal, as shown by the graph of FIG. 14. In particular, the dotted line charts the delivery of the oxygen pulse, which starts at approximately 0.6 seconds (approximately 0.2 seconds after inspiration) and lasts for about 0.3 seconds or less, meaning that most of the oxygen has been delivered within the first half second after the patient inspiration.

The task of delivering most oxygen within the first half second of inspiration becomes progressively more difficult as larger volume pulses need to be delivered. The components of device 21 described above include features which enhance the oxygen delivery profile and generally allow for rapid delivery even of high volume oxygen pulses at the outset of inspiration, generally within about the first one-half second. This is generally accomplished by providing for main valve 47 to reciprocate or open and close very rapidly, in a so-called "snap action", which action permits a rapid, high-volume spike of oxygen to be quickly delivered at the onset of inspiration.

Such rapid reciprocation of main valve 47 involves reciprocation of moveable element 91 within chamber 93 of main valve 47. When main valve 47 is closed, moveable element 91 is in its upper position, as oriented in the drawings, in which its upper side 99 seals chamber inlet 95 and chamber outlet 97 and thereby closes off reservoir 45 from delivery. When sealed in this manner, pressure line 105 exerts pressure across substantially the whole area of lower or opposite side 100 of moveable element 91, whereas upper side 99 is only acted upon by pressure across a relatively smaller area corresponding to the area of chamber inlet 95. The difference in pressure exerted over surface areas on opposite side 99, 100 of moveable element 91 maintains moveable element 91 sealed in its upper position.

Upon inhalation, however, the force exerted on bottom side 100 of piston 91 begins to reduce, as pressure line 105 is gradually relieved, that is, vented to atmosphere in this embodiment. When the pressure exerted on side 100 of moveable element 91 drops sufficiently, the pressure on opposite, upper side 99 is sufficient to slightly unseal chamber inlet 95, that is, the previous seal of reservoir 45 is "cracked open". As soon as upper side 99 slightly unseals from chamber inlet 95, substantially all of the surface area of the side 99 becomes exposed to pressure of gas storage in reservoir 45, rather than the more reduced area of inlet 95 previously exposed to such pressure when upper side 99 was sealed thereagainst. The sudden increase of surface area rapidly increases the downward force (as oriented by the drawing) exerted on moveable element 91, which, in turn, causes element 91 to reciprocate or "snap" downward rapidly.

In such downward or lower position, bottom side 100 of moveable element 91 seals pressure line 105. By virtue of the fact that pressure line 105 has a pressure inlet 101 with a smaller surface area than upper surface 99, when inlet 101 is sealed, a relatively smaller force is exerted against bottom side 100 than against opposite side 99, which pressure imbalance keeps pressure line 105 sealed during most of the oxygen delivery.

Once the pressure from reservoir 45 has been sufficiently reduced by delivery of oxygen therefrom, the force exerted against upper side 99 is reduced so that the opposing force exerted on lower side 100 slightly unseals lower side 100 from pressure inlet 101. Again, as explained previously, this slight unsealing immediately expands the surface area of lower side 100 over which pressure from pressure line 105 acts. Such expansion of surface area, in turn, rapidly increases the upward force (as oriented in relation to the drawings), which, in turn, reciprocates moveable element 91 rapidly and upwardly in a "snap action", after which it again seals in the upper position to close off oxygen delivery from reservoir 45.

The rapid reciprocation of main valve 47 delivers the steep, oxygen-rich pulses shown in the graph of FIG. 14 at the beginning moments of inspiration, when most desirable.

In the preferred embodiment, by about the end of the first tenth of a second, device 21 senses inspiration by the patient, such "sensing" corresponding to the small bump in the dotted line, which indicates sensing valve 49 has opened. By about the lapse of the second tenth of a second, air under the main valve (adjacent to lower side 100) escapes through port 115 to relieve pressure line 105 and main valve 47 unseals slightly from chamber inlet 95, which then causes main valve 47 to "snap open." Between about the second tenth of a second and the third tenth of a second, the delivery of a pulse of oxygen from reservoir 45 commences and lasts for about three tenths of a second. At about 0.45 seconds, sense diaphragm 119 closes and begins pressurizing under main valve 47. After about five tenths of a second, the pressure differential has been reduced sufficiently in main valve 47 so that moveable element 91 slightly unseals from pressure inlet 101, after which it "snaps" or reciprocates rapidly upwardly to close reservoir 45.

Because gas continually flows into reservoir 45 through variable-rate passage 63 of the flow-rate selector 43, when reservoir outlet 87 is sealed by piston 91, reservoir 45 becomes pressurized with gas entering through reservoir inlet 85.

When the person once again inhales, the volume of pressurized gas stored in reservoir 45 is released and main valve 47 is opened, whereupon the delivery cycle described above is repeated. The foregoing cycle repeats indefinitely so long as gas remains in gas source B.

Pressure line 105 is preferably equipped with a constriction selected to reduce the rate of repressurization at the bottom of piston 91. By slowing the rate of repressurization, reservoir outlet 87 remains open for an amount of time sufficient to deliver the desired oxygen pulse before closing.

The need to deliver oxygen for longer periods is more prevalent when higher volume minute rates of oxygen delivery are needed. Accordingly, smaller vent orifices 79 are interposed in vent to atmosphere 127 when correspondingly larger variable rate orifices 75 are interposed in variable rate passage 63.

The differently sized orifices which can be selectively interposed in variable rate passage 63 are referred to as different "settings" on the device, which would be associated with indications (not shown) on the knob 83. In this preferred embodiment, the variable rate orifices 75 and vent orifices 79 correspond as follows, expressed in inches: setting 1 has a 0.004 variable rate orifice 75 and a 0.012 vent orifice 79, setting 2 has a 0.0062 variable rate orifice 79 and a 0.013 vent orifice, setting 3 has a 0.0077 variable rate orifice 79 and a 0.015 vent orifice, setting 4 has a 0.0092 variable rate orifice 79 and a 0.017 vent orifice, and setting 5 has a 0.00101 variable rate orifice 79 with a 0.08 vent orifice.

There is sometimes a need to deliver oxygen in a constant, uninterrupted manner. Device 21 accomplishes such "continuous flow" deliver by a suitable positioning of the orifice plate, in which variable rate orifice 79 is 0.0092.

Figure 12:
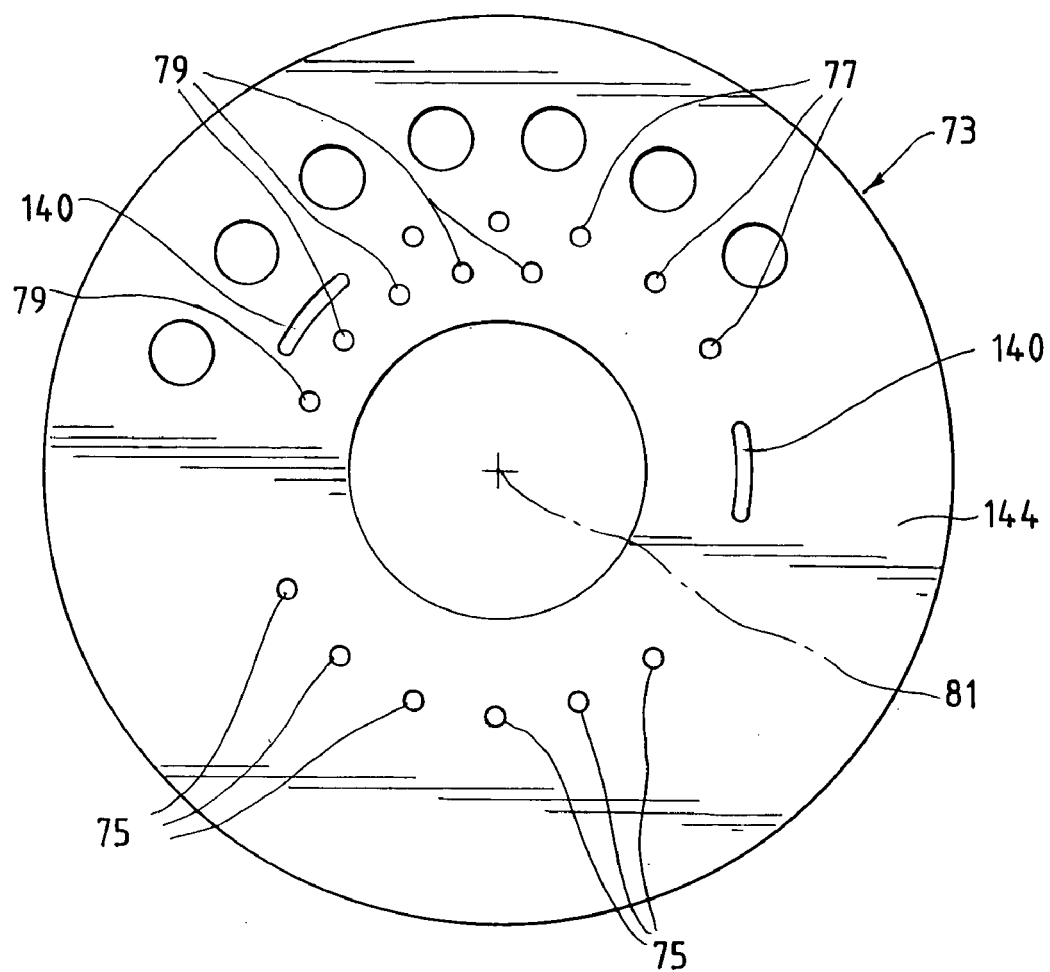
Figure 13:
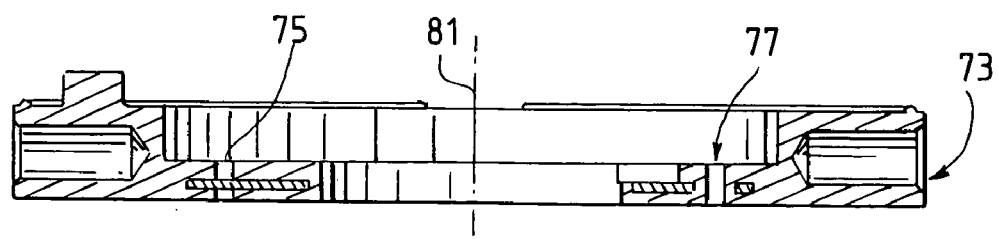

Referring to FIGS. 11 and 12, orifice plate 73 has been equipped with elongated cavities or grooves 163, which are located at the same radial distance from center 81 as constant rate orifices 77. Cavities 163 do not extend transversely through the entire width of orifice plate 73, but rather are formed to extend only partly through plate 73 from planar service 144 (FIG. 12) thereof. Planar surface 144, in turn, opposes disk 151 of plate 139. Accordingly, when orifice plate 73 is rotated so that grooves 163 are aligned with pressure passage 65, pressure passage 65 is blocked, whereas grooves 163 permit pressure line 105 to communicate with the ambient. (FIG. 5). By maintaining pressure line 105 in communication with the ambient, it is assured that flow through device 21 will remain continuous, since main valve 47 remains open.

There are two grooves 163, one of which provides for constant flow as outlined above. The second groove 163 serves as a "failsafe" to avoid undesirable pressure buildup within device 21 in the event of a malfunction when the flow is turned off through such device.

Main body 31 of conserving device 21 has the various device components arranged therein to reduce the length, size and bulk of device 21. For example, a plate 139, best seen in FIGS. 7-10, includes upper and lower discs 151, 153 held in longitudinal, spaced relationship from each other by an intermediate element 140. Element 140 is generally box shaped, with one vertical wall proximate to the circumference of the discs 151, 153 along a portion of the arcs of such circumferences. Chamber 93 of main valve 47 is defined in one portion of element 140, whereas delivery line 107, pressure line 105, and vent to atmosphere 127 are substantially defined in another portion of element 140 to one side of chamber 93. This side-by-side arrangement of chamber 93 and its various related passages avoids increasing the overall length of conserving device 21.

Similarly, reservoir 45 is defined between the two discs 151, 153 and extends in a "C" shape surrounding element 140. Discs 151, 153 are sealed against the inner wall of housing 25 to create the appropriate air-tight conditions in reservoir 45. Again, the location of reservoir 45 in a surrounding relationship to element 140 avoids increasing the overall length of conserving device 21.

Disc 151 opposes orifice plate 73. Accordingly, disc 151 has reservoir inlet 85 defined therein at a location to correspond to variable rate passage 63 (FIG. 4) to receive oxygen into the reservoir at a selected minute volume. Disc 153, in turn, opposes sensing valve 49 and also faces delivery outlet 33. Accordingly, delivery passage 107 has a terminal portion exiting through disc 153.

Figure 3:
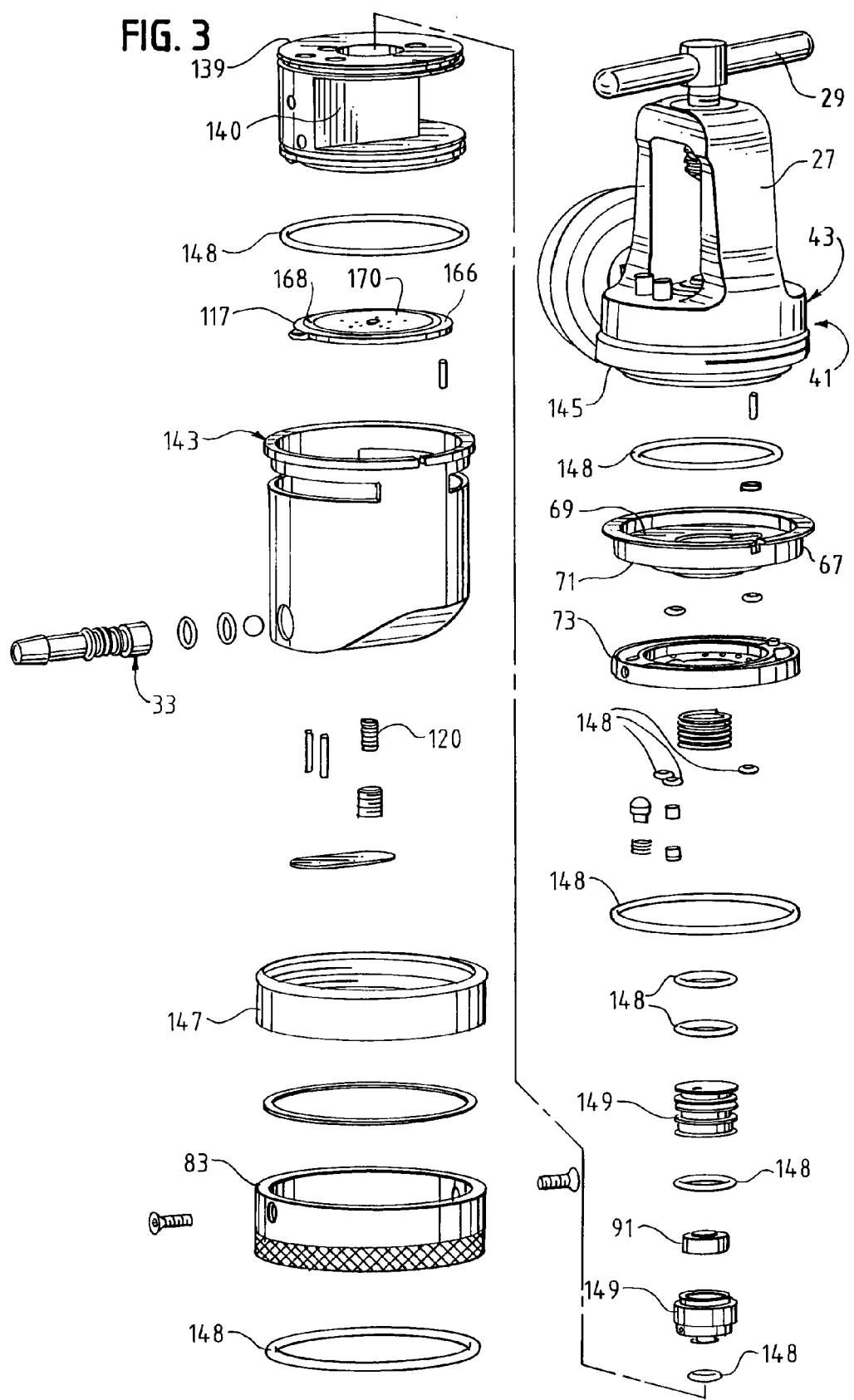
FIG. 3 is an exploded perspective view of the conserving device of FIG. 2.

Regulator 41, flow-rate selector 43, and plate 139 are secured to each other along longitudinal axis 37. In this preferred embodiment, regulator 41, flow-rate selector 43, and plate 139 are each substantially cylindrical and have central axes mounted coaxially with longitudinal axis 37 of main body 31. As best seen in FIG. 3, main body 31 includes an end cap 143, the outer surface of which forms a substantial part of external housing 25 of device 21. End cap 43 is secured to a corresponding base member 145 by a collar 147.

Suitable openings and seals 148 are interposed between subcomponents of device 21 in a manner known in the art to foster the necessary pneumatic communications as well as to isolate passages and chambers from each other as required. The counterbore 135 preferably has an effective diameter of 15–18 thousandths of an inch, and the constriction in the pressure line 105 is preferably about 2 thousandths of an inch.

Piston 91 of main valve 47 is preferably and primarily formed of polymeric material and is received in a piston insert 149. Piston insert 149, in turn, is received in a friction fit in bore 161 in plate 139, which bore 161 corresponds to chamber 93 of main valve 47.

The port 115 of sensing valve 49 preferably has a size of 0.008 inches. Sensing element 117 preferably comprises a diaphragm with the following characteristics: a 1.43" diameter ring 166 (FIG. 3) is formed at the outer edge thereof. The ring 166 is 0.050" thick at this point and acts as a seal and a foundation. Connected to this ring is a convolute 168 that acts as a hinge. A center plate 170 extends inwardly from convolute 168. A seat 172 (FIGS. 4–6) is secured to center plate 170 and located to open or close port 115. One side of seat 172 opposes port 115, while the other side of seat 172 is formed into a spring boss 174 which receives spring 120 thereon. The diaphragm is secured within sensing chamber 119 by the ring 166, the convolute allows the center plate to move in and out, and the seat opens and closes the 0.008 orifice. Inspiration overcomes the force of spring 120 to open the seat 172.

The check element of check valve 51 preferably comprises a nylon check ball with a diameter of 0.187 inches received in chamber 137 of diameter of 0.196 inches.

Plate 139, orifice plate 73, base 145, end cap 143, flow-rate selector 43, and regulator 41, are generally made of machined metal, preferably aluminum. Non-metallic plugs, seals and the like are provided in a manner generally known to the art to interconnect or isolate the components of device 21.

Figure 15:
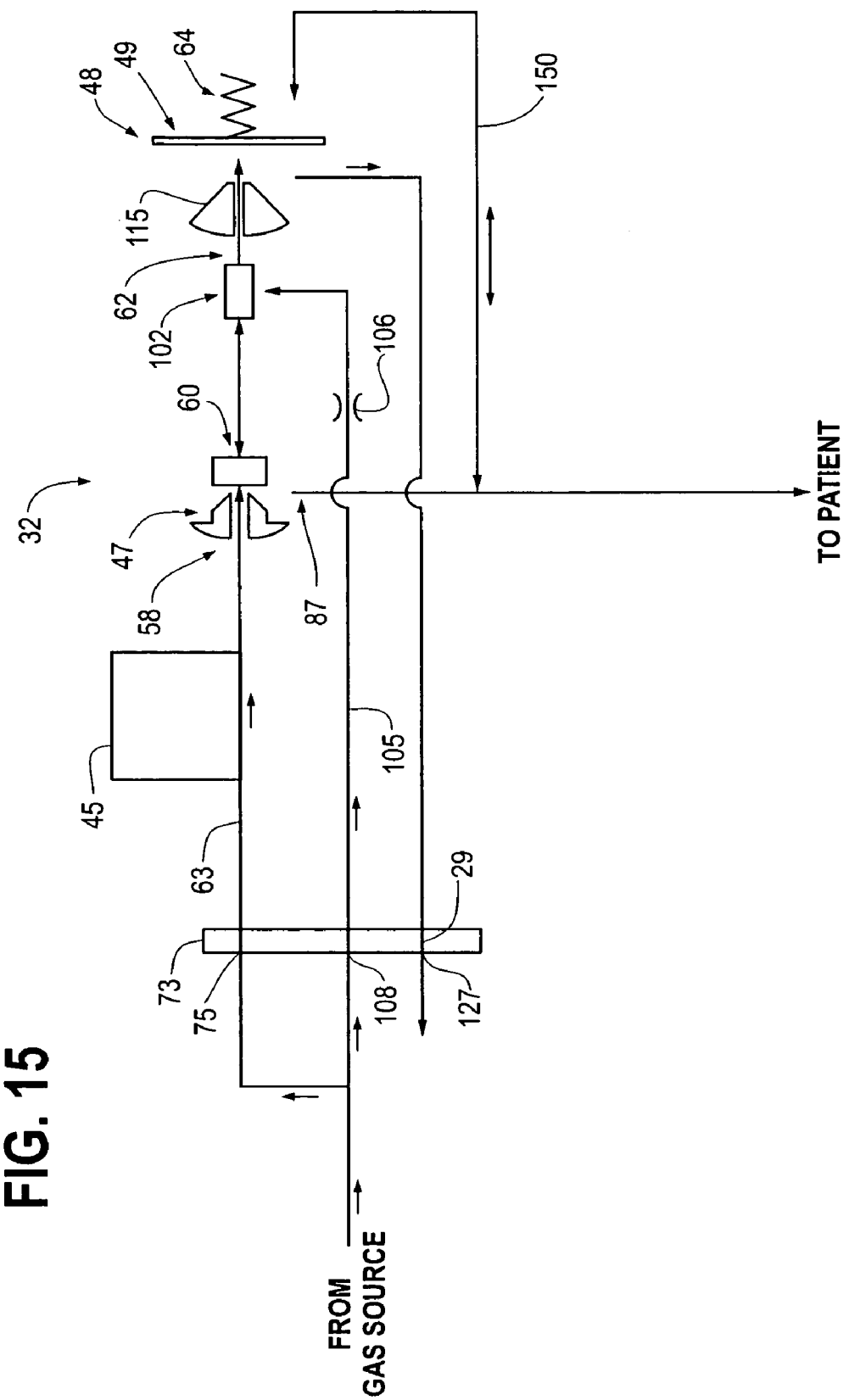
FIG. 15 is a schematic representation of the conserving device of FIGS. 1–13.

The foregoing, preferred embodiment of device 21 is shown schematically in FIG. 15, emphasizing the general pneumatic connection (also referred to herein as "pneumatic communication") of the components. Main valve 47 and sensing valve 49 each have control portions 60, 64, respectively, which are associated with closing, opening, or otherwise controlling the corresponding operations of valves 47, 49. Valves 47, 49 also have operational portions 58, 62, respectively, more associated with the functions of the oxygen conserving device itself and, more particularly, the handling of gas or air flowing through it or to it. The source of regulated oxygen shown is pneumatically connected to operational portion 58 of main valve 47. In this embodiment, the gas from the source passes through a suitable restriction (in this case a selected one of orifices 75 of orifice plate 73). The gas flow is then pneumatically connected via passage 63 to reservoir 45, which reservoir 45, in turn, is in pneumatic communication with delivery system 32, including main valve 47. Thus, the pressure of the gas from reservoir 45 acts on operational portion 58 of main valve 47.

The control portion 60 of main valve 47 is pressurized by a suitable pneumatic connection 105 between the gas source and main valve 47. In this embodiment, gas emanating from the gas source passes through orifice plate 73, through a suitable restriction 106, and into a region 102 in communication with portion 60 of main valve 47. The gas in region 102 is likewise in pneumatic communication with sensing system 48, including sensing valve 49 and port 115. The control portion 64 of sensing valve 49 is in pneumatic communication with delivery line C (FIG. 1) and the person or patient. The operational portion 62 of sensing valve 49 communicates with region 102 and the control portion 60 of main valve 47. Thus, the pressure of the gas in region 102 is not only present on control portion 60 of main valve 47, but also on operational portion 62 of sensing valve 49. In the embodiment illustrated in FIGS. 4–6, region 102 includes intermediate passage 103 (FIG. 5) and pressure inlet 101 (FIG. 4).

In FIGS. 15–19, operational portions 58, 62 and control portions 60, 64 of valves 47, 49, respectively, have been shown schematically for ease of reference on opposite "sides" of valves 47, 49, and it should be understood that such positioning of portions 58, 60, 62, and 64 does not necessarily correspond to actual physical locations.

In the 0.5 to 1.0 second delivery cycle typical for the illustrated embodiment of device 21, upon inhalation, the region 102 vents relatively quickly to atmosphere, with or without a restriction on such vent-to-atmosphere 127. Such emptying of region 102 creates a relatively immediate pressure imbalance between portions 58 and 60 of main valve 47, which imbalance opens main valve 47 to dispense gas from the gas source through device 21, and out delivery outlet 33, in this embodiment using the intermediary of a reservoir 45.

Pneumatic connection 150 between the delivery system 32 and the sensing system 48 is provided so that the gas, when dispensed, causes the delivery system 32 to interrupt the dispensing of the gas thereafter. More particularly, referring to the schematic of FIG. 15, the operational portion 58 of main valve 47 is suitably pneumatically connected to control portion 64 of sensing valve 49 to transmit a portion of the gas exiting main valve 47 to control portion 64 of the sensing valve 49. In this embodiment, pneumatic connection 150 extends between outlet 87 of main valve 47 and the control portion 64 of sensing valve 49 so that gas exiting main valve 47 closes sensing valve 49 shortly after delivery of the oxygen pulse to the patient has commenced. Again, "shortly after" should be understood in the context of a delivery cycle, which cycle, in this embodiment, is preferably about 0.5 seconds to about 1.0 seconds.

Although such pneumatic connection 150 is shown in FIGS. 4–6 to comprise delivery passage 107 and sensing passage 50, it should be noted that the above described pneumatic connection 150 and resulting pneumatic communication between the delivered gas and the sensing system 48 can assume any of a variety of forms, so long as sufficient pressure is communicated to sensing system 48 to close sensing valve 49 at the appropriate time after oxygen has been dispensed. Thus, while the embodiment illustrated in FIGS. 4–6 includes a restriction at opening 103 to delay the transmission of pressure to sensing valve 49, such as a check valve 51, such a restriction or structure is not necessary to embody the principles of the present invention, and any number of alternatives to pneumatic connection 150 are likewise suitable to transmit the appropriate pressure to sensing valve 49. Thus, pneumatic connection 150 can be sized and dimensioned to exclude a check valve 51 and to exclude intermediate restrictions, so long as, upon dispensing of the gas, sufficient gas or pressure is transmitted by delivery system 32 to sensing system 48. Likewise, although sensing passage 50 is shown having one end connected proximate to delivery outlet 33, other connection locations or configurations are likewise equally suitable to receive a portion of the delivered oxygen.

Having reached the point in the gas delivery cycle that sensing valve 47 has been reclosed by a portion of gas exiting main valve 49, region 102 begins to repressurize. The size of region 102 is one variable which influences how quickly the gas control system 90 repressurizes and closes main valve 47 to end oxygen pulse delivery. In other words, region 102 acts as a "timing reservoir" in the sense that, depending on its size, it will repressurize such that the balance of pressures on portions 58, 60 of main valve 47 is sufficient to urge main valve 47 to the closed position to end gas delivery.

The pneumatic connections between components of device 21, and the various flow rates and pressures associated with such components and their connections, can be accomplished using a variety of differently sized passages, orifices, and areas, depending on the particular application requirements. For example, it has been found preferable, though by no means required, to configure passage 105 to control pressures within device 21 which, in turn, enhances the emptying and refilling of region 102. More particularly, when sense valve 49 opens in response to inhalation, since it is important for region 102 to experience sufficient pressure drop to open main valve 47, it is likewise important that region 102 not become refilled with oxygen from pressure line 105 too quickly. This means that pressure line 105 must be suitably sized or restricted so that gas from the gas source does not flow too soon, or at too high a rate, into region 102 upon the emptying of region 102 through orifice 115. One way to accomplish this is by forming a suitable restriction 106 in pressure line 105 pneumatically "upstream" from region 102.

Similarly, upon delivery of oxygen through main valve 47, in certain embodiments, pressure between orifice plate 73 and the operational portion 58 of main valve 47 decreases sufficiently to draw gas away from line 105, which would hamper the refilling of region 102. In such embodiments, it is thus preferable to maintain a sufficient amount of gas and pressure within the system in a manner and location to enable region 102 to refill as required to close main valve 47 at the appropriate time after gas pulse delivery. In the embodiment illustrated in FIGS. 4–6 and schematically in FIG. 15, this is accomplished by including a further valve or restriction 108 in line 105. Such restriction 108 is further upstream from restriction 106 and thus acts to "trap" or maintain sufficient gas and pressure in line 105 between such restrictions for the desired refilling of region or "timing reservoir" 102, and the corresponding cycling of main valve 47.

The restriction 108 may not be needed if line 105 or other components of device 21 are sized or "tuned" to maintain gas and pressure sufficient to refill region 102. When needed, restriction 108 can assume any number of forms, including an insert with an aperture therein, a portion with a smaller diameter, a check valve, and the like. Restriction 108, like the other apertures, passages, and regions of device 21, are interdependent and thus can be "tuned" relative to each other to create the desired gas pulse and associated timing of the delivery system components. In this embodiment, restriction 108 is interposed in line 105 by virtue of constant rate orifice 77 (FIGS. 11–12) in orifice plate 73, although alternate locations outside orifice plate 73 are likewise suitable.

Figure 16:
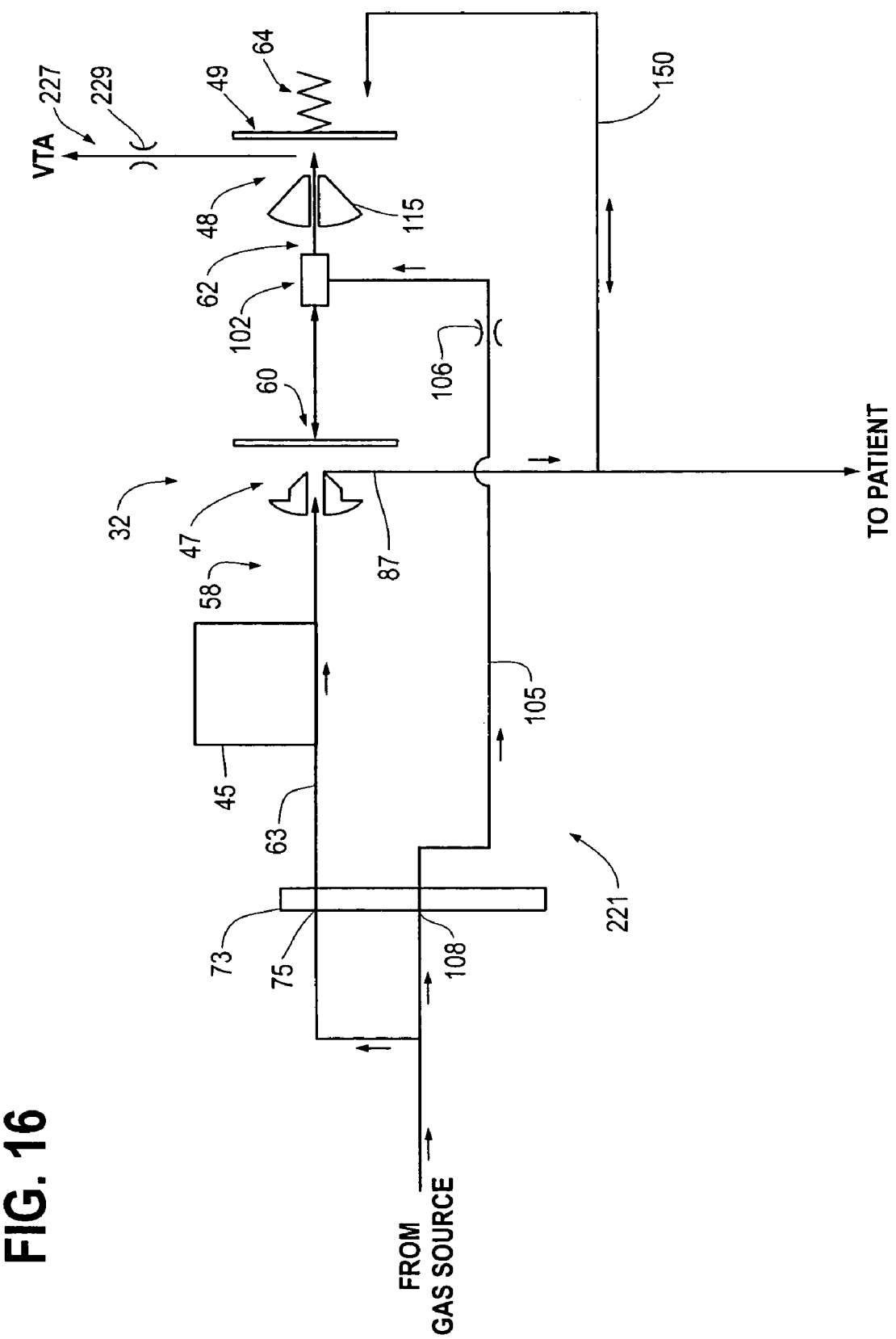
FIG. 16 is a schematic representation of a conserving device according to a first alternative embodiment of the present invention.

FIG. 16 is a schematic showing another preferred embodiment of the invention in the form of an oxygen conserving device 221. Oxygen conserving device 221 is generally similar to oxygen conserving device 21 described above, with certain differences now described. The movable element of main valve 47 is in the form of a diaphragm rather than piston 91 (FIG. 3) of the previous embodiment, and vent to atmosphere 227 includes a restriction 229 at a location other than the orifice plate.

It has been found advantageous, but by no means required, for sensing element 117 of device 221 to have an area which is many times greater in area than the area of opening 149 in port 115. Among the many suitable area ratios which would be suitable, a ratio of about 1,000 to 1 between the areas of sensing element 117 and port 115, respectively functions in the device 221 described herein. With such a sensing element 117, other variables of device 221 can be "tuned" within the following ranges:

Reservoir 45 ranging in size from about 0.2 cubic inches to 2 cubic inches; timing reservoir 102 ranging in size from about 0.1 cubic inches to 0.2 cubic inches; restriction 106 ranging in size from about 0.0005 to 0.002 inches in diameter; and a vent-to-atmosphere restriction ranging from about 0.005 to 0.030 inches in diameter.

The oxygen savings resulting from the conserving functions of the conserving device can be expressed in terms of amount of oxygen expended with the conserver to achieve a given oxygen saturation, versus the amount required for such saturation in a corresponding "continuous" oxygen delivery environment. Although the principles of the current invention are applicable to a conserving device that achieves any amount of oxygen conservation, in the case of device 221 by way of example, there is approximately a 5 to 1 savings. Otherwise stated, the device 221 will supply 80% less oxygen (or 20% of the amount otherwise supplied by comparable continuous flow), but achieve the same or better oxygen saturation of the user's blood. It should be noted that the calculated savings depend on certain assumptions related to device settings, breathing patterns, saturation, or other similar variables.

Figure 17:
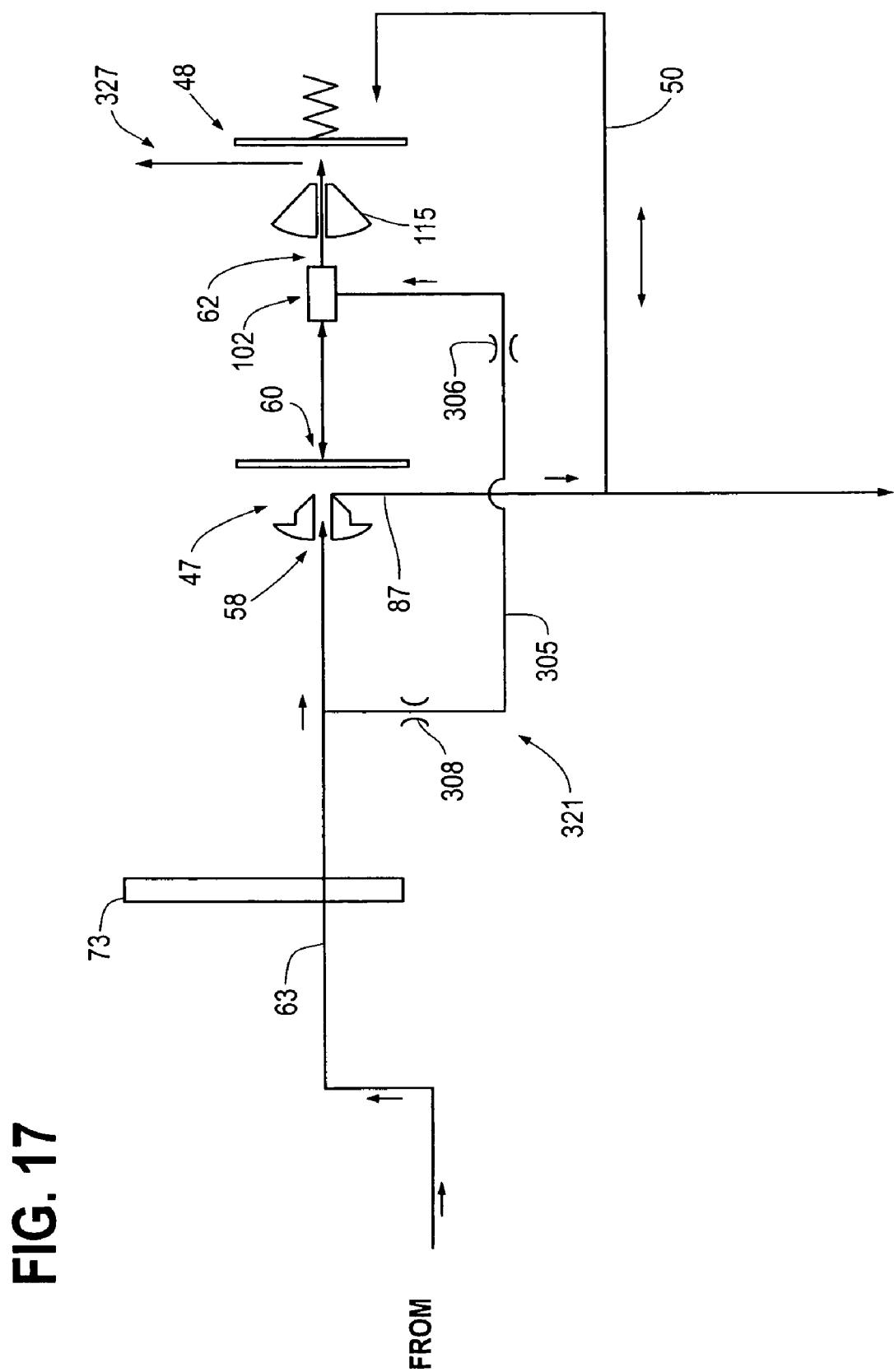
FIG. 17 is a schematic representation of a conserving device according to a second alternative embodiment of the present invention.
Figure 18:
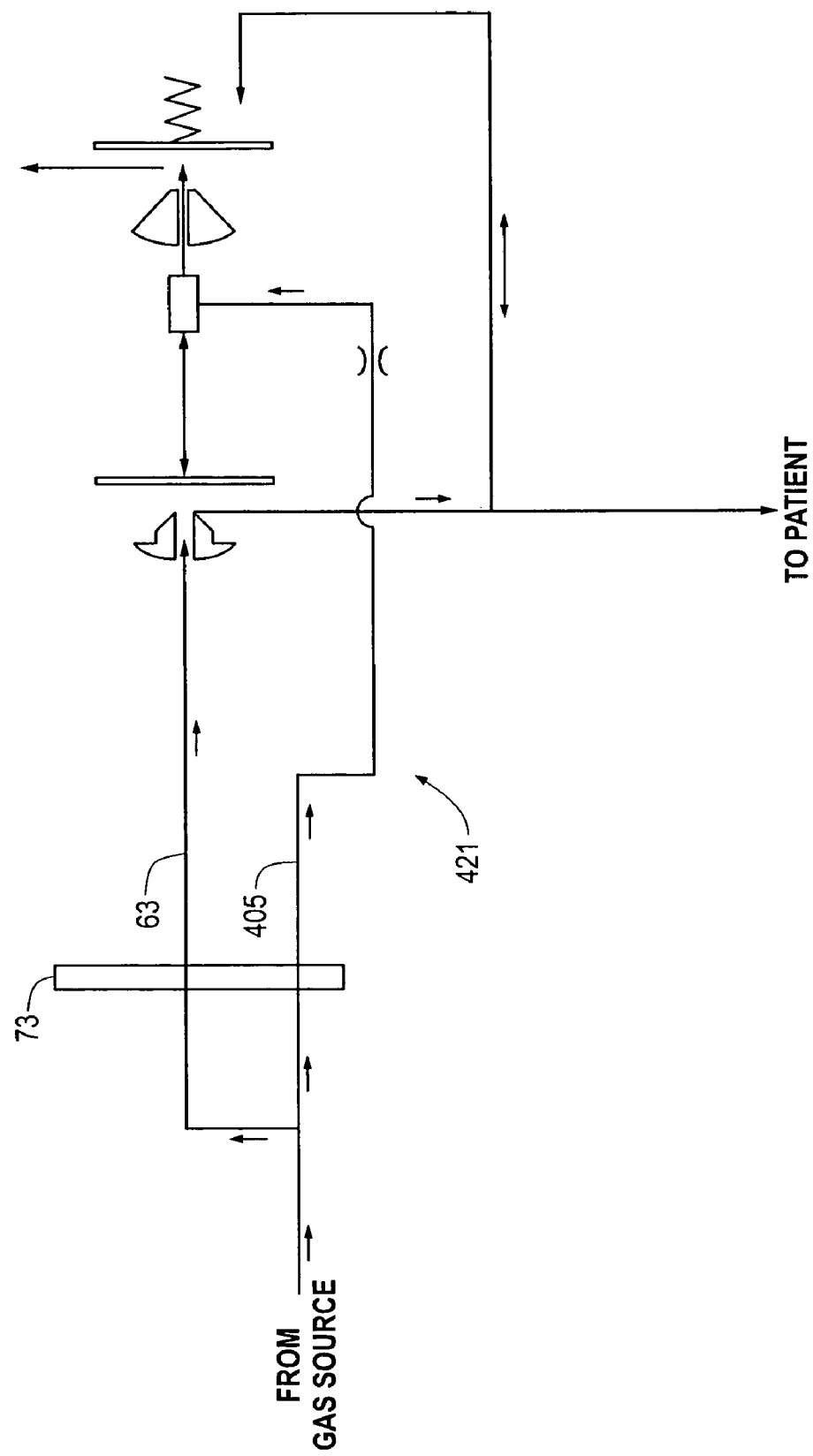
FIG. 18 is a schematic representation of a third alternative embodiment according to the present invention.

Another preferred embodiment of the invention is shown schematically as oxygen conserving device 321 in FIG. 17. Although the operating principles of oxygen conserving device 321 are the same as those for the previously described embodiments, the sizes, dimensions, and other variables relating to the pneumatic connections of the components have been "tuned" differently in this embodiment. Unlike the previous embodiments, gas from the gas source does not charge or enter a volume functioning as a supply reservoir within device 321. Rather, the gas flows from its source into passage 63 or other suitable pneumatic connection, passes through a selected one of orifices 75, and acts on the operational portion 58 of main valve 47. Unlike previous embodiments, a pneumatic connection in the form of pressure line 305 does not pass through orifice plate 73, but rather line 305 comes from the gas supply after orifice plate 73 through a first suitably sized or "tuned" restriction 308, a second restriction 306, and into region 102 in communication with the control portion 60 of main valve 47. As in previous embodiments, the gas at the control portion 60 of main valve 47 is likewise in pneumatic communication with sensing system 48. As such, the pressure of the gas in region 102 acts on operational side 62 of the sensing valve 49.

As in the previous embodiments, upon inhalation, sensing valve 59 opens to allow gas to flow out region 102 through port 115 and exit device 321 through vent-to-atmosphere 327. This, in turn, as described previously, opens main valve 47 to deliver a pulse of oxygen from the gas source to the patient. As before, delivered oxygen acts to close sensing valve 48, timing reservoir 102 refills, and main valve 47 closes to end the oxygen delivery. In this embodiment, the delivered pulse is sufficiently sized to achieve desired oxygen saturation without needing a reservoir upstream of main valve 47. Another distinction of this embodiment is that vent-to-atmosphere 327 does not include an area which functions as a restriction (beyond the restricting effect of vent-to-atmosphere 327 itself being a passage through which oxygen is necessarily confined while exiting the device 321).

Still further variations in the sizes, dimensions, and configurations of the pneumatic connections and components are possible within the scope of the invention to create still further alternative embodiments. For example, referring now to FIG. 18, oxygen conserving device 421 is similar to oxygen conserving device 321 of the previous embodiment, except the pneumatic connection from the gas source is directed through orifice plate 73, rather than coming from the gas source without passing through such orifice plate. Such configuration permits orifice plate 73 to be rotated to a suitable position to cut off pressure line 405 from its gas source, thereby placing oxygen conserving device 421 in so-called "continuous mode" (which mode was likewise available in devices 21, 221 discussed above). One skilled in the art can readily configure any of the conserving devices of the present invention to operate in "continuous mode" by a variety of techniques which put pressure on main valve 47 in such a way that it remains open to permit such continuous delivery.

Referring now to FIG. 19, another alternative embodiment, oxygen conserving device 521 makes use of reservoir 45. Pressure line 105 and pneumatic passage 63 are combined in this embodiment, meaning that a suitable restriction in orifice plate 73 not only supplies reservoir 45, but also supplies the required flow of gas and pressure into region 102.

It would be appreciated by those skilled in the art that still further alternative embodiments can be devised incorporating the principles of the present invention, by selecting appropriate aperture sizes, passage restrictions, volumes, or chambers or regions to hold pressurized gas, as discussed previously, with the result that oxygen gas is conserved in a pneumatic system by delivering pulses of oxygen in response to inhalation.

In general terms, in the preferred embodiments discussed above, the delivery of the oxygen pulse creates sufficient back pressure on the control portion of sensing valve 59, so that, at an appropriate time after delivery of the oxygen pulse commences, the balance of forces closes sensing valve 59. Such closure, in turn, augments the repressurization of region 102 on the operational portion of sensing valve 59. The amount of time to repressurize region 102 sufficiently to close main valve 47 and interrupt oxygen delivery depends on the balance of pressures on the opposing sides of main valve 47.

This balance of pressures is influenced by device variables related to the size and configuration of certain passages, apertures, restrictions, regions, orifices, outlets, and the like. These include, without limitation, the size and configuration of the pressure line 105, 305 from the gas source to region 102, including the size of its restriction (if any), whether it passes through the orifice plate, and, if so, whether it is restricted by such passage through the orifice plate 73. Further variables determining the balance of pressures and the associated timing of main valve 47 include, without limitation, the size and configuration of the vent-by-atmosphere 127, the sensing passage 50, and the restrictions associated with such passages, if any, as well as the sizes of reservoir 45 (if any), region 102, movable element 91 of main valve 47, element 117 of sensing valve 49, and the pressure area differentials between the open and closed states of such valves 47, 49.

The foregoing variables and others are selected or "tuned" in device 21 to deliver pulses of oxygen pneumatically in response to inhalation, such pulse being sufficient to achieve corresponding oxygen saturation levels in the user, while also generating back pressure to end oxygen delivery and conserve oxygen.

Referring to the reservoir-less device 321 (FIG. 17), for example, suitable dimensions for appropriate oxygen pulses include a region 102 from about 0.15 to about 0.5 cubic centimeters, a pressure area differential between about 50 psi and 10 psi, ranging from about 1 to 1 to about 1 to 4, a vent-to-atmosphere 327 having a size ranging between about 0.04 to about 0.08 inches, restrictions 306, 308 ranging between about 0.0006 inches and 0.0012 inches respectively, and a check valve.

In addition to the advantages apparent from the foregoing description, the inventive conserving device delivers a pulse of gas on demand, in accordance with generally accepted gas delivery profiles, and interrupts the flow of gas when no longer needed, thus lengthening the useful life of a finite source of pressurized gas.

As a further advantage, the device according to the present invention can be used with a variety of common single-lumen cannulas.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A conserving device for use in delivering gas from a source of gas through a gas line, the conserving device comprising:
   a main valve operable in an open position for the gas to exit the main valve and in a closed position in which the gas exit is interrupted;
   a sensing valve operable to open in response to a pressure drop and to close upon sufficient return of pressure;
   a first pneumatic connection between the source of gas and the main valve to bias the main valve toward the closed position;
   a second pneumatic connection between the main valve and the sensing valve to receive a portion of the gas exiting the main valve and transmit a sufficient pressure to the sensing valve to close the sensing valve, whereupon the gas from the first pneumatic connection closes the main valve, interrupting delivery of the gas to the patient substantially independently of exhalation, whereby the gas is delivered intermittently and is conserved; and an orifice plate, the orifice plate having a plurality of orifices disposed in spaced relation thereon, a selected one of the orifices positioned between, and in pneumatic communication with, the source of gas and the main valve, the selected orifice corresponding to a rate of flow of the gas.

2. The device of claim 1, wherein the first pneumatic connection includes a pressure line.

3. The device of claim 2, wherein the pressure line further includes a restriction therein sized to retard the time taken to close the main valve and interrupt the flow of gas.

4. The device of claim 3, wherein the pressure line includes a port opened and closed by operation of the sensing valve, and further comprising a vent in pneumatic communication with the port to allow gas flowing from the port to escape to the ambient.

5. The device of claim 4, wherein the vent further includes a passage with at least one restriction therein sized to retard the escape of the gas to the ambient and the corresponding time taken to close the sensing valve.

6. The device of claim 1, wherein the second pneumatic connection comprises a sensing passage.

7. The device of claim 6, wherein the sensing passage communicates between the gas line and the sensing valve to open the sensing valve in response to inhalation.

8. The deice of claim 1, wherein the first pneumatic connection includes a region which depressurizes to open the main valve and repressures to close the main valve.

9. The device of claim 1, wherein the second pneumatic connection includes a portion having a smaller cross-sectional area than adjacent areas to restrict the flow of gas therethrough.

10. The device of claim 1, further comprising a pressure regulator, the pressure regulator including
    a regulator inlet adapted to attach to the source of gas;
    means for reducing the pressure of the source of gas to a delivery pressure; and
    a regulator outlet for delivering the gas at the delivery pressure, the regulator outlet in pneumatic communication with the selected orifice of the orifice plate.

11. The device of claim 10, wherein the regulator and the orifice plate are secured in series.

12. The device of claim 1, wherein the first pneumatic connection further includes a portion passing through the orifice plate.

13. The device of claim 1, wherein the main valve comprises a chamber and an element received in the chamber and movable therein to cause the main valve to close and open when predetermined pressures exist within the chamber.

14. The device of claim 13, wherein the element movable within the chamber comprises a diaphragm.

15. The device of claim 1, further comprising a reservoir having an inlet for receiving the gas into the reservoir and an outlet for discharging the gas from the reservoir, the outlet being in pneumatic communication with the main valve, whereby the opening of the main valve allows the gas to exit the outlet of the reservoir, and the closing of the main valve prevents gas from exiting the reservoir.

16. The device of claim 15, wherein the first pneumatic connection includes a portion extending from the reservoir to the main valve.

17. The device of claim 1, wherein the first pneumatic connection does not have any portion passing through the orifice plate.

18. The device of claim 1, wherein the first pneumatic connection includes a portion extending from a location downstream of the orifice plate to the main valve.

19. The device of claim 18, wherein the portion extending from the location downstream includes a restriction defined therein.

20. A conserving device for use in delivering gas to a person from a source of gas, the conserving device comprising:
    a delivery system adapted to be coupled in pneumatic communication with the source of gas and operable to dispense gas intermittently from the source of gas to the person;
    a sensing system adapted to be in pneumatic communication with the person to detect a pressure drop upon inhalation by the person, the sensing system also in pneumatic communication with the delivery system to cause the delivery system to dispense the gas in response to the sensing system's detecting the pressure drop;
    wherein the delivery system and the sensing system are in pneumatic communication so that the gas, when dispensed, causes the delivery system to interrupt the dispensing of the gas substantially independently of exhalation by the person;
    wherein the delivery system comprises a main valve operable in an open position and a closed position, the gas exiting the main valve when in the open position; and
    wherein the sensing system comprises a sensing valve, the sensing valve operable to open in response to inhalation, the sensing valve in communication with the main valve and operable to close in response to the gas exiting the main valve; and
    wherein the main valve and the sensing valve have respective operational and control portions, the operational portion of the main valve adapted to receive the gas from the gas source for intermittent dispensing through the main valve, the control portion of the sensing valve adapted to be in communication with the person, and wherein the control portion of the main valve and the operational portion of the sensing valve are in communication with each other;
    further comprising first and second pneumatic connections associated with the main valve and the sensing valve, the first pneumatic connection extending from the gas source to the control portion of the main valve and to the operational portion of the sensing valve, the second pneumatic connection configured to communicate a portion of the gas dispensed from the main valve to the control portion of the sensing valve to close the sensing valve, the first pneumatic connection configured to increase the pressure on the main valve sufficiently o close the main valve after the sensing valve closes, wherein the first pneumatic connection comprises a pressure line extending from the gas source; and
    further comprising an orifice plate having orifices capable of being positioned to restrict the flow of gas from the gas source, and wherein the pressure line comprises a passage extending through the orifice plate.

21. The device of claim 20, wherein the first pneumatic connection has been configured to increase the pressure on the control portion of the main valve at a rate selected so that a desired amount of the gas is dispensed out the main valve before the control portion of the main valve is exposed to pressure sufficient to close the main valve.

22. The device of claim 21, wherein the first pneumatic connection includes a restriction.

23. The device of claim 20, wherein the first pneumatic connection is configured to maintain a threshold pressure during dispensing of the gas.

24. The device of claim 20, wherein the second pneumatic connection includes a sensing passage having one end in communication with the gas exiting the main valve and another end in communication with the sensing valve.

25. The device of claim 24, wherein the main valve has a delivery passage, and wherein the sensing passage is in communication with the delivery passage and the control portion of the sensing valve.

26. The device of claim 25, wherein the second pneumatic connection further includes a restriction formed therein to restrict the flow of gas to the control portion of the sensing system.

27. The device of claim 26, further comprising a reservoir for holding a volume of gas for delivery to the person, the reservoir having an inlet for receiving the gas from the gas source and an outlet in communication with the delivery system to dispense the gas from the reservoir when the main valve is opened.

28. A pneumatic oxygen conserving device for use in delivering oxygen to a person from a source of oxygen, the conserving device comprising:
    delivery system adapted to be coupled in pneumatic communication with the source of oxygen and operable to dispense oxygen intermittently from the source of oxygen to the person; and
    a sensing system adapted to be in pneumatic communication with the person to detect a pressure drop upon inhalation by the person, the sensing system also in pneumatic communication with the deliver system to cause the delivery system to dispense the oxygen in response to the sensing system's detecting the pressure drop, the sensing system further adapted to cause the device to interrupt oxygen delivery substantially independently of exhalation by the person.

29. The device of claim 28, wherein the sensing system includes a sensing valve operable to open or close as a function of forces exerted thereon.

30. The device of claim 29, wherein the sensing system includes a spring adapted to exert a force to bias the valve toward the closed position.

31. The device of claim 29, wherein the sensing system includes a pneumatic connection to the gas dispensed by the delivery system to bias the sensing valve toward the closed position.

32. The consenting device of claim 28,
    wherein the delivery system comprises a main valve operable in an open position and a closed position, the gas exiting the main valve when in the open position; and
    wherein the sensing system comprises a sensing valve, the sensing valve operable to open in response to inhalation, the sensing valve in communication with the main valve and operable to close in response to the gas exiting the main valve.

33. The conserving device of claim 32, wherein the main valve and the sensing valve have respective operational and control portions, the operational portion of the main valve adapted to receive the gas from the gas source for intermittent dispensing through the main valve, the control portion of the sensing valve adapted to be in communication with the person, and wherein the control portion of the main valve and the operational portion of the sensing valve are in communication with each other.

34. The device of claim 33, further comprising first and second pneumatic connections associated with the main valve and the sensing valve, the first pneumatic connection including the gas source, the control portion of the main valve, and the operational portion of the sensing valve, the second pneumatic connection configured to communicate a portion of the gas dispensed from the main valve to the control portion of the sensing valve to close the sensing valve, the first pneumatic connection configured to increase the pressure on the main valve sufficiently to close the main valve after the sensing valve closes.

35. The device of claim 34, further comprising a region located between the control portion of the main valve and the operational portion of the sensing valve, wherein the region is in communication with the gas source via the first pneumatic connection, the region having a corresponding volume, the closing of the main valve being a function of the time to fill said volume to a sufficient pressure.

36. The device of claim 34, wherein the first pneumatic connection comprises a pressure line.

37. The device of claim 34, wherein the first pneumatic connection has been configured to increase the pressure on the control portion of the main valve at a rate selected so that a desired amount of the gas is dispensed out the main valve before the control portion of the main valve is exposed to pressure sufficient to close the main valve.

38. The device of claim 37, therein the first pneumatic connection includes a restriction.

39. The device of claim 34, wherein the first pneumatic connection is configured to maintain a threshold pressure during dispensing of the gas.

40. The device of claim 34, wherein the second pneumatic connection comprises a sensing passage having one end in communication with the gas exiting the main valve and another end in communication with the sensing valve.

41. The device of claim 10, wherein the main valve has a delivery passage, and wherein the sensing passage is in communication with the delivery passage and the control portion of the sensing valve.

42. The device of claim 41, wherein the second pneumatic connection further includes a restriction formed therein to restrict the flow of gas to the control portion of the sensing system.

43. The device of claim 34, further comprising a reservoir for holding a volume of gas for delivery to the person, the reservoir having an inlet for receiving the gas from the gas source and an outlet in communication with the delivery system to dispense the gas from the reservoir when the main valve is opened.

* * * * *